(12) United States Patent
Schweinsberg

(10) Patent No.: US 8,795,642 B2
(45) Date of Patent: Aug. 5, 2014

(54) HAIR TREATMENT AGENTS COMPRISING POLYETHER-MODIFIED ORGANIC COMPOUNDS AND HAIR STYLING POLYMERS

(75) Inventor: Matthias Schweinsberg, Hamburg (DE)

(73) Assignee: Henkel AG & Co. KGaA, Dusseldorf (DE)

( * ) Notice: Subject to any disclaimer, the term of this patent is extended or adjusted under 35 U.S.C. 154(b) by 15 days.

(21) Appl. No.: 13/363,546

(22) Filed: Feb. 1, 2012

(65) Prior Publication Data

US 2012/0128617 A1 May 24, 2012

Related U.S. Application Data

(63) Continuation of application No. PCT/EP2010/061046, filed on Jul. 29, 2010.

(30) Foreign Application Priority Data

Aug. 4, 2009 (DE) .......................... 10 2009 028 209

(51) Int. Cl.
| | | |
|---|---|---|
| *A61K 8/00* | (2006.01) | |
| *A61K 8/18* | (2006.01) | |
| *A61K 8/73* | (2006.01) | |
| *A61K 8/81* | (2006.01) | |
| *A61Q 5/06* | (2006.01) | |
| *A61Q 5/04* | (2006.01) | |
| *A61Q 5/00* | (2006.01) | |
| *A61Q 9/00* | (2006.01) | |
| *A61Q 17/04* | (2006.01) | |

(52) U.S. Cl.
USPC ...... 424/70.1; 424/59; 424/70.16; 424/70.13; 424/70.2

(58) Field of Classification Search
USPC .................... 424/59, 70.1, 70.16, 70.13, 70.2
See application file for complete search history.

(56) References Cited

U.S. PATENT DOCUMENTS

| | | |
|---|---|---|
| 3,753,968 A | 8/1973 | Ward et al. |
| 6,235,913 B1 | 5/2001 | Raths et al. |
| 7,332,466 B2 | 2/2008 | Schmid et al. |
| 2010/0209613 A1 | 8/2010 | Rong et al. |

FOREIGN PATENT DOCUMENTS

| | | |
|---|---|---|
| AU | 730455 B2 | 5/2000 |
| DE | 3139438 A1 | 4/1983 |
| DE | 19756454 C1 | 6/1999 |
| DE | 10240757 A1 | 7/2003 |

*Primary Examiner* — Mina Haghighatian
*Assistant Examiner* — Luke Karpinski
(74) *Attorney, Agent, or Firm* — Ingrassia Fisher & Lorenz, P.C.

(57) ABSTRACT

Hair treatment agents that, in addition to at least one hair-setting polymer, additionally contain polyether-modified organic compounds having at least three polyether substituents, the polyethers comprising a polyalkylene chain made up of ethylene oxide units or ethylene oxide units and propylene oxide units, having a maximum proportion of 50 wt % propylene oxide units based on weight of the polyoxyalkylene chain.

20 Claims, No Drawings

HAIR TREATMENT AGENTS COMPRISING POLYETHER-MODIFIED ORGANIC COMPOUNDS AND HAIR STYLING POLYMERS

CROSS REFERENCE TO RELATED APPLICATIONS

This application is a continuation of International Patent Application No. PCT/EP2010/061046 filed 29 Jul. 2010, which claims priority to German Patent Application No. 10 2009 028 209.2 filed 4 Aug. 2009, both of which are incorporated herein by reference.

The present invention relates to hair treatment agents that, besides at least one hair-setting polymer, additionally contain specific polyether-modified organic compounds; and to the use of said hair treatment agent for temporary hairstyling, and to a corresponding hair treatment method.

Hair treatment agents that serve for permanent or temporary shaping of the hair play an important role in cosmetics. Temporary conformations that are intended to yield good hold without impairing the hair's healthy appearance, for example its shine, can be achieved, for example, using hair sprays, hair waxes, hair gels, hair foams, blow-dry waves, etc.

Corresponding agents for temporary shaping usually contain synthetic polymers as a shape-imparting component. Preparations that contain a dissolved or dispersed polymer can be applied onto the hair by means of propellant gases or by way of a pump mechanism. Hair gels and hair waxes in particular, however, are generally not applied directly onto the hair but rather distributed in the hair by means of a comb or the hands.

The most important property of an agent for the temporary deformation of keratinic fibers, hereinafter also called a "styling agent," is to impart the strongest possible hold to the treated fibers in the shape that is generated. If the keratinic fibers involved are human hairs, terms also used are a strong "hairstyle hold" or a high "degree of hold" of the styling agent. The hairstyle hold is determined substantially by the nature and quantity of the synthetic polymer used, although the further constituents of the styling agent can also have an influence.

In addition to a high degree of hold, styling agents must also meet a large number of further requirements. These can be subdivided roughly into properties on the hair; properties of the particular formulation (e.g., properties of the foam, gel, or sprayed aerosol); and properties that relate to the handling of the styling agent, the properties on the hair being of particular importance. Moisture resistance, low tack, and a balanced conditioning effect may be mentioned in particular. In addition, a styling agent should be universally usable for, if possible, all types of hair.

A high degree of hold is often undesirably associated with a highly brittle hairstyle. The hair treated with the corresponding styling agent is stiff, brittle, and appears to be unnaturally solid. As a result, it also feels rough and poorly cared for. In addition, in the aforesaid cases the polymer film left behind by the agents upon application to the hair is so inflexible that it breaks under stress. This results in the formation of so-called film plaques, i.e. residues that detach upon movement of the hair and give the impression that the user of the corresponding styling agent has dandruff.

A further problem is that the product consistency of such products is evaluated negatively by the user, since these products are viewed as viscous, tacky, and difficult to apply.

The object of the present invention was therefore to make available an agent for the temporary deformation of keratinic fibers that is notable for a very high degree of hold with no need to sacrifice flexibility and a conditioned hair feel, as well as pleasant product haptics.

The document WO-A1-20091024450 describes star-shaped polyether-containing compounds that are utilized in agents for cleaning surfaces and that inhibit re-soiling of the cleaned substrate.

It has now been discovered, surprisingly, that styling products having a high degree of hold and a pleasant well-cared-for feel in the hair can be made available by incorporating a combination of specific ingredients into the agents.

A first subject of the invention is therefore a cosmetic agent containing, in a cosmetically acceptable carrier, a) polyether-modified organic compounds that comprise at least three polyether substituents, the polyethers encompassing a polyoxyalkylene chain made up of ethylene oxide units or of ethylene oxide units and propylene oxide units, having a maximum proportion of 50 wt % propylene oxide units based on the weight of the polyoxyalkylene chain, and b) at least one film-forming and/or setting polymer.

Polyether substituents" are understood as a chemical structural fragment that encompasses a polyoxyalkylene chain made up of ethylene oxide units or of ethylene oxide units and propylene oxide units, having a maximum proportion of 50 wt % propylene oxide units based on the weight of the polyoxyalkylene chain, which is covalently bonded directly, or via a structural fragment imparting a chemical bond, to an organic compound.

An "ethylene oxide unit" is to be understood for purposes of the present invention as a unit of the general formula (1)

$$*-CH_2-CH_2-O-* \qquad \text{formula (1),}$$

and a "propylene oxide unit" is to be understood for purposes of the present invention as a unit of the general formula (2)

$$*-CH_2-CH(CH_3)-O-* \qquad \text{formula (2).}$$

In accordance with the above formulas (1) and (2) and all subsequent formulas, a chemical bond having the symbol "*" is a free valence of the corresponding structural fragment.

"Organic compounds" are understood as chemical compounds based on a hydrocarbon structural fragment. Corresponding hydrocarbon structural fragments are derived from linear, branched, cyclic, or heterocyclic hydrocarbons, all of which can respectively be saturated, unsaturated, or aromatic.

"Polyether-modified organic compounds" are understood according to the present invention as organic compounds that are modified with polyether-containing substituents, the polyether substituents each constituting a chemical bond to the organic compound that is to be modified.

If the polyalkylene chain of the polyether substituents contains ethylene oxide units and propylene oxide units, the maximum proportion of propylene oxide units is then preferably equal to 40 wt % and particularly preferably to a maximum of 30 wt %, based on the weight of A.

The polyether-modified organic compounds are contained in the agents according to the present invention preferably in a quantity from 0.01 to 10.0 wt %, particularly preferably from 0.1 to 2.0 wt %, very particularly preferably 0.2 to 1.0 wt %, based in each case on the weight of the entire agent.

The aforesaid polyether-modified organic compounds having at least three polyether substituents are preferably chosen from at least one compound of the general formula (PE-1)—

(PE-1)

wherein
A is a polyoxyalkylene chain made up of ethylene oxide units or of ethylene oxide units and propylene oxide units, having a maximum proportion of 50 wt % propylene oxide units based on the weight of A,
K and K' are, mutually independently, a connectivity chosen from a covalent bond or from a molecule fragment having two free valences,
T is a molecule fragment encompassing at least one substituent chosen from
anionic residue,
—$Si(OR)_x(R')_{3-x}$ residue
wherein R and R' are, mutually independently, a ($C_1$ to $C_4$) alkyl group (particularly methyl or ethyl), and x is 1, 2, or 3,
Q is an organic structural fragment derived from linear, branched, cyclic, or heterocyclic hydrocarbons, all of which may respectively be saturated, unsaturated, or aromatic,
n is a whole number from 3 to 64, particularly 3, 4, 5, 6, 7, or 8.

"A" in accordance with formula (PE-1) is preferably a structural fragment of formula (A1)

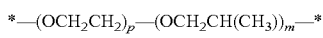  (A1)

wherein
p is a whole number from 1 to 500,
m is a whole number from 0 to 500, and
the structural fragment of formula (A1) has a maximum proportion of 50 wt % propylene oxide units, based on weight of the structural fragment (A1). The ethylene oxide units and propylene oxide units in accordance with formula (PE-1) or in accordance with formula (A1) can be statistically distributed or distributed in gradient fashion or can be present in at least two blocks.

If group A of the compounds according to formula (I) (or according to all subsequent formulas containing A) is a polyoxyalkylene chain made up of ethylene oxide units and propylene oxide units, the maximum proportion of propylene oxide units is then preferably a maximum of 40 wt % and more preferably a maximum of 30 wt %, based on the weight of A.

Residues K or K' in accordance with formula (PE-1) preferably are, mutually independently, a covalent bond, an oxy group, a ($C_1$ to $C_6$) alkylene group, an imino group, or at least one of the following connectivities (K1) to (K10)—

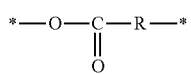 (K1)

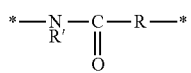 (K2)

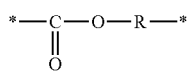 (K3)

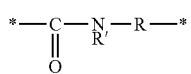 (K4)

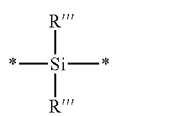 (K5)

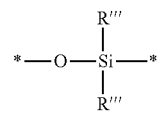 (K6)

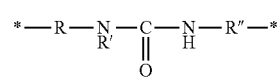 (K7)

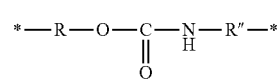 (K8)

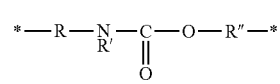 (K9)

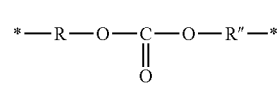 (K10)

wherein
R and R" are, mutually independently, methylene, ethane-1,2-diyl, propane-1,2-diyl, propane-1,3-diyl, butane-1,2-diyl, butane-1,3-diyl, butane-1,4-diyl, or phenylene,
R' is a hydrogen atom or a ($C_1$ to $C_4$) alkyl group,
R''' is, mutually independently, a ($C_1$ to $C_4$) alkyl group or an aryl group.

T in accordance with formula (PE-1) preferably is
an anionic structural fragment
or
a —$Si(OR)_x(R')_{3-x}$ residue, wherein R and R' are, mutually independently, a ($C_1$ to $C_4$) alkyl group (particularly methyl or ethyl), and x is 2 or 3 (preferably triethyoxysilyl).

Very particularly preferably, the structural fragment —K-T according to formulae (PE-1a) to (PE-1f) is a

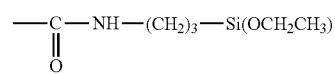

group.

Q preferably is a corresponding organic residue having 2 to 30 carbon atoms, preferably 2 to 20 carbon atoms.

Q is preferably derived from glycerol, monosaccharide, disaccharide. Very particularly preferably, Q is derived from a compound chosen from sorbitol, 1,5-anhydrosorbitol, 1,4-anhydrosorbitol, inositol, xylitol, mannitol, gluconolactone, glucuronic acid, 1,2,6-hexanetriol, hydroxyethylsorbitol, phytantriol, hydroxypropylphytantriol, lactitol, maltitol, pentaerythritol, polyglycerol-3, glucose, fructose, galactose, ribose, xylose, mannose, sucrose, cellobiose, gentiobiose, isomaltose, lactose, lactulose, maltose, maltutose, melibiose, trehalose, nigerose, palatinose, rutinose, arabinose.

Very particularly preferred polyether-modified organic compounds are chosen from at least one compound of formula (PE-1a) or (PE-1b) or (PE-1c) or (PE-1d) or (PE-1e) or (PE-1f) or mixtures thereof:

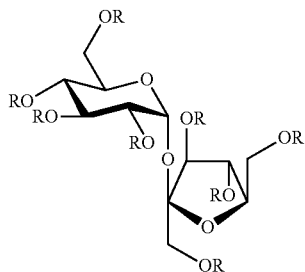
(PE-1a)

wherein at least three groups R are a —(CH$_2$CH$_2$O)$_p$—(CHCH$_3$CH$_2$O)$_m$—K-T group, and the remaining groups R are a hydrogen atom or a —K-T group, wherein, mutually independently, p is a whole number from 1 to 500, m is a whole number from 0 to 500, and p and m have a ratio to one another such that a maximum proportion of 50 wt % (preferably a maximum of 40 wt %, particularly preferably a maximum of 30 wt %) propylene oxide units, based on the weight of the corresponding polyoxyalkylene chain, exists, K is a connectivity chosen from a covalent bond or from a molecule fragment having two free valences, T is a molecule fragment having at least one substituent chosen from anionic residue, —Si(OR)$_x$(R')$_{3-x}$ residue wherein R and R' are, mutually independently, a (C$_1$ to C$_4$) alkyl group (particularly methyl or ethyl), and x is 1, 2, or 3;

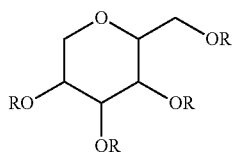
(PE-1b)

wherein at least three groups R are a —(CH$_2$CH$_2$O)$_p$—(CHCH$_3$CH$_2$O)$_m$—K-T group, and the remaining groups R are a hydrogen atom or a —K-T group, wherein, mutually independently, p is a whole number from 1 to 500, m is a whole number from 0 to 500, and p and m have a ratio to one another such that a maximum proportion of 50 wt % (preferably a maximum of 40 wt %, particularly preferably a maximum of 30 wt %) propylene oxide units, based on the weight of the corresponding polyoxyalkylene chain, exists, K is a connectivity chosen from a covalent bond or from a molecule fragment having two free valences, T is a molecule fragment having at least one substituent chosen from anionic residue, —Si(OR)$_x$(R')$_{3-x}$ residue wherein R and R' are, mutually independently, a (C$_1$ to C$_4$) alkyl group (particularly methyl or ethyl), and x is 1, 2, or 3;

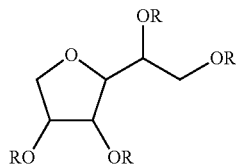
(PE-1c)

wherein at least three groups R are a —(CH$_2$CH$_2$O)$_p$—(CHCH$_3$CH$_2$O)$_m$—K-T group, and the remaining groups R are a hydrogen atom or a —K-T group, wherein, mutually independently, p is a whole number from 1 to 500, m is a whole number from 0 to 500, and p and m have a ratio to one another such that a maximum proportion of 50 wt % (preferably a maximum of 40 wt %, particularly preferably a maximum of 30 wt %) propylene oxide units, based on the weight of the corresponding polyoxyalkylene chain, exists, K is a connectivity chosen from a covalent bond or from a molecule fragment having two free valences, T is a molecule fragment having at least one substituent chosen from anionic residue, —Si(OR)$_x$(R')$_{3-x}$ residue wherein R and R' are, mutually independently, a (C$_1$ to C$_4$) alkyl group (particularly methyl or ethyl), and x is 1, 2, or 3;

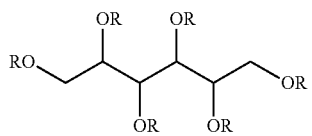
(PE-1d)

wherein at least three groups R are a —(CH$_2$CH$_2$O)$_p$—(CHCH$_3$CH$_2$O)$_m$—K-T group, and the remaining groups R are a hydrogen atom or a —K-T group, wherein, mutually independently, p is a whole number from 1 to 500, m is a whole number from 0 to 500, and p and m have a ratio to one another such that a maximum proportion of 50 wt % (preferably a maximum of 40 wt %, particularly preferably a maximum of 30 wt %) propylene oxide units, based on the weight of the corresponding polyoxyalkylene chain, exists, K is a connectivity chosen from a covalent bond or from a molecule fragment having two free valences, T is a molecule fragment having at least one substituent chosen from anionic residue, —Si(OR)$_x$(R')$_{3-x}$ residue wherein R and R' are, mutually independently, a (C$_1$ to C$_4$) alkyl group (particularly methyl or ethyl), and x is 1, 2, or 3; and

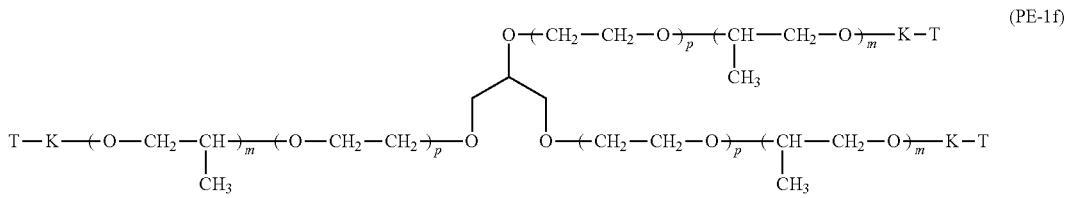

wherein, mutually independently, p is a whole number from 1 to 500, m is a whole number from 0 to 500, and p and m have a ratio to one another such that a maximum proportion of 50 wt % (preferably a maximum of 40 wt %, particularly preferably a maximum of 30 wt %) propylene oxide units, based on the weight of the corresponding polyoxyalkylene chain, exists, K is, mutually independently, a connectivity chosen from a covalent bond or from a molecule fragment having two free valences, T is, mutually independently, a molecule fragment having at least one substituent chosen from
anionic residue,
—Si(OR)$_x$(R')$_{3-x}$ residue
wherein R and R' are, mutually independently, a ($C_1$ to $C_4$) alkyl group (particularly methyl or ethyl), and x is 1, 2, or 3.

The ethylene oxide units and propylene oxide units can be statistically distributed or distributed in gradient fashion or can be present in at least two blocks.

The previously preferred groups K and T apply to formulae (PE-1a) to (PE-1f). Very preferably, the structural fragment —K-T according to formulae (PE-1a) to (PE-1f) is a

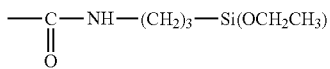

group.

Those cosmetic agents containing, in a cosmetically acceptable carrier, (a) polyether-modified organic compounds that are obtained by reacting
  (i) organic compounds containing at least three residues selected from a hydroxy group and/or amino group (in particular: from a hydroxy group, primary amino group, secondary amino group; particularly preferably hydroxy group(s)), with
  (ii) at least 3 molar equivalents of at least one polyether of formula (I)

wherein
A is a polyoxyalkylene chain made up of ethylene oxide units or of ethylene oxide units and propylene oxide units, having a maximum proportion of 50 wt % propylene oxide units based on the weight of A,
K and K' are, mutually independently, a connectivity chosen from a covalent bond or from a molecule fragment having two free valences,
T is a molecule fragment encompassing at least one substituent chosen from anionic residue,
—Si(OR)$_x$(R')$_{3-x}$ residue
wherein R and R' are, mutually independently, a ($C_1$ to $C_4$) alkyl group (particularly methyl or ethyl), and x is 1, 2, or 3, Y is a group reactive with respect to a hydroxy group or amino group,
and
(b) at least one film-forming and/or setting polymer
are preferred according to the present invention.

The indication of molar equivalents refers to the quantity of substance of the organic compound used.

The preferred embodiments recited under formula (PE-1) apply to the residues A, K, K', and T.

The residue Y according to formula (I) is preferably—
an isocyanate function,
a *—Si(R)$_x$(R')$_{3-x}$ group
wherein R and R' are, mutually independently, a ($C_1$ to $C_4$) alkyl group (particularly methyl or ethyl), and x is 1, 2, or 3,
a *—Si(OR)$_x$(R')$_{3-x}$ group
wherein R is a halogen atom (preferably chlorine or bromine) and R' is, mutually independently, a ($C_1$ to $C_4$) alkyl group (particularly methyl or ethyl), and x is 1, 2, or 3,
a T-K—C(O)—O—C(O)—* group, wherein T and K are defined in accordance with formula (I),
a *—C(O)-Hal group, wherein Hal is chlorine or bromine,
an epoxy group,
a formyl group.

Polyether-modified organic compounds of this embodiment are present in agents according to the present invention preferably in a quantity from 0.01 to 10.0 wt %, more preferably from 0.1 to 2.0 wt %, and particularly preferably 0.2 to 1.0 wt %, based on weight of the entire agent.

Polyethers of formula (I) have a molar mass preferably from 1 to 200 kDa, particularly preferably from 1 to 10 kDa.

Polyethers usable in the context of the invention for manufacturing polyether-modified organic compounds of component (a) are obtainable by reacting at least one compound of formula (II)—

wherein
A is a polyoxyalkylene chain made up of ethylene oxide units or of ethylene oxide units and propylene oxide units, having a maximum proportion of 50 wt % propylene oxide units based on the weight of A,
X and X' are, mutually independently, a structural fragment containing an OH, NH$_2$, or NHR group,
with at least 2 equivalents of a compound of formula (III)—

wherein
Y is a group that is reactive with respect to OH, NH$_2$, NHR, NR$_2$,

K is a connectivity chosen from a covalent bond or from a molecule fragment having two free valences, T is a molecule fragment having at least one substituent chosen from
anionic residue,
—Si(OR)$_x$(R')$_{3-x}$ residue
wherein R and R' are, mutually independently, a (C$_1$ to C$_4$) alkyl group (particularly methyl or ethyl), and x is 1, 2, or 3.

Molar equivalents refer to the quantity of substance of the compound(s) of formula (II) that are used.

According to the above manufacturing method for manufacturing compounds of formula (I), the following are used, for example, as compounds of formula (II): dihydroxy-terminated polyoxyalkylenediols, diamino-terminated polyoxyalkylenediamines, monohydroxy-/monoamine-terminated polyoxyalkylene monol/monoamines, monohydroxy-/monoalkoxy-terminated polyoxyalkylene monols, or monoamino-/monoalkoxy-terminated polyoxyalkylene monoamines, among which the diamines and diols are preferred.

Residues X and X' of formula (II) preferably are, mutually independently, OH, NH$_2$, and NHR, particularly preferably OH and NH$_2$.

Residue R in the NHR, NR$_2$, and OR groups of formula (III) preferably is a linear or branched alkyl group having 1 to 10, preferably 1 to 6 carbon atoms.

The number-average molecular weight of the compound of formula (II) is preferably 100 to 50,000 g/mol, more preferably 500 to 30,000 g/mol, even more preferably 1000 to 20,000, even better 2000 to 18,000 g/mol, and can be ascertained, as in the Examples section, by terminal group determination.

The preferred embodiments recited under formula (PE-1) apply to the residues A, K, K', and T.

Those cosmetic agents containing, in a cosmetically acceptable carrier, (a) polyether-modified organic compounds obtained by reacting
(i) organic polyether polyol compounds having
at least three polyoxyalkylene chains made up of ethylene oxide units or of ethylene oxide units and propylene oxide units, having a maximum proportion of 50 wt % propylene oxide units based on the weight of the polyoxyalkylene chain,
at least three hydroxy groups
with
(ii) at least 3 molar equivalents of at least one compound of formula (III)

$$Y—K-T \quad (III)$$

wherein
Y is a group that is reactive with respect to OH, NH$_2$, NHR, NR$_2$,
K is a connectivity selected from a covalent bond or from a molecule fragment having two free valences,
T is a molecule fragment having at least one substituent chosen from
anionic residue,
—Si(OR)$_x$(R')$_{3-x}$ residue
wherein
R and R' are, mutually independently, a (C$_1$ to C$_4$) alkyl group (particularly methyl or ethyl), and x is 1, 2, or 3;
and
(b) at least one film-forming and/or setting polymer
are furthermore preferred according to the present invention.

Corresponding polyether polyols usable according to the present invention in step (i) include VORANOL®, TERRALOX®, SYNALOX®, and DOWFAX® of the Dow Chemical Corporation, SORBETH® of Glyco Chemicals Inc., GLUCAM® of Amerchol Corp., or Lupranol® and Pluronic® of BASF.

It is preferable to use in the context of this embodiment, as a compound of formula (III), at least one compound of the general formula (III-1)—

$$Y—K—Si(OR)_x(R')_{3-x} \quad (III-1),$$

wherein
Y is a group that is reactive with respect to OH, NH$_2$, NHR, and/or NR$_2$ (in particular, an isocyanate group, a halogen atom, a carboxylic anhydride group, a halocarbonyl group (particularly chlorocarbonyl), an epoxy group, a formyl group),
K is defined as in formula (I) (or like the aforementioned preferred connectivities),
R is a (C$_1$ to C$_4$) alkyl group or a (C$_2$ to C$_4$) acyl group (particularly ethyl or methyl),
R' is a (C$_1$ to C$_4$) alkyl group (particularly ethyl or methyl), and
x is 1, 2, or 3.

Included among the compounds of general formula (III-1) are all functional silane derivatives capable of reacting with Y groups of formula (III-1). Examples are acrylate silanes such as (3-acryloxypropyl)trimethoxysilane, (acryloxymethyl)triethoxysilane, and (acryloxymethyl)methyldimethyloxysilane, isocyanatosilanes such as (3-isocyanatopropyl)trimethoxysilane, (3-isocyanatopropyl)triethoxysilane, (isocyanatomethyl)methyldimethoxysilane, and (isocyanatomethyl)trimethoxysilane, aldehyde silanes such as triethoxysilylundecanal and triethoxysilylbutyraldehyde, epoxy silanes such as (3-glycidoxypropyl)trimethoxysilane, anhydride silanes such as 3-(triethoxysilyl)propylsuccinic acid anhydride, halogen silanes such as chloromethyltrimethoxysilane, 3-chloropropylmethyldimethoxysilane, and tetraethyl silicate (TEOS), commercially obtainable, for example, from Wacker Chemie GmbH (Burghausen, Germany), Gelest Inc. (Morrisville, Pa., USA), or ABCR GmbH & Co KG (Karlsruhe, Germany), or can be manufactured in accordance with known methods. Isocyanatosilanes or anhydride silanes are particularly preferred. Upon complete reaction of all the hydroxy termini with isocyanatosilanes, completely silylated polyethers are obtained. In such a case the K group contains only the atomic group that is located between the isocyanate group and the silyl group in the initial isocyanatosilane. Upon complete reaction of all hydroxy termini with anhydride silanes, for example, 3-(triethoxysilyl)propylsuccinic acid anhydride, completely silylated polyethers are likewise obtained. In such a case the K' group contains only the atomic group that is located between the anhydride group and the silyl group in the initial anhydride silane.

If residues X and X' in general formula (II) are OH, NH$_2$, or NHR, the reaction with the compounds of general formula (III) or (III-1) then usually occurs either with release of the HY compound—for example, as in the case of reacting an OH group with a monohalosilane (K=direct bond)—or with addition—for example, in the case of reacting an OH group with an isocyanatoalkylsilane (formation of a urethane).

Residues X and X' of formula (II) are, mutually independently, preferably OH, NH$_2$, and NHR, particularly preferably OH and NH$_2$.

Residue R in the NHR, NR$_2$, and OR groups of formula (III-1) preferably is a linear or branched alkyl group having 1 to 10, by preference, 1 to 6 carbon atoms.

Upon reaction between the compounds of formula (I) and the compounds of formula (II), at least one hydrogen atom, preferably up to four hydrogen atoms, of the OH and/or $NH_2$ groups is/are each reacted with a molecule of the compound of general formula (II), resulting in at least monosilylated polyethers, and in the case of the diamino compounds of general formula (I), up to quadruply silylated polyethers.

Very particularly preferred polyethers for manufacturing polyether-modified organic compounds according to the present invention are chosen from at least one compound of formulae (I-1a) or (I-1b)

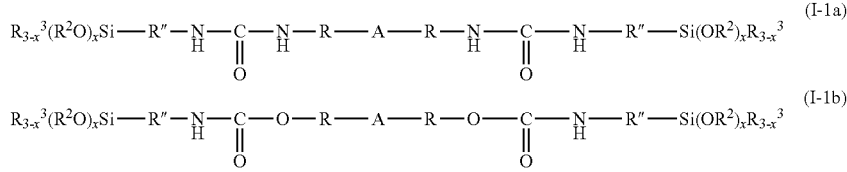

wherein

A is a polyoxyalkylene chain made up of ethylene oxide units or of ethylene oxide units and propylene oxide units, having a maximum proportion of 50 wt % propylene oxide units based on the weight of A, R and R" are, mutually independently, methylene, ethane-1,2-diyl, propane-1,2-diyl, propane-1,3-diyl, butane-1,2-diyl, butane-1,3-diyl, butane-1,4-diyl, phenylene, $R^1$ is a ($C_1$ to $C_6$) alkyl group, a hydrogen atom, or an $R^3_{3-x}(R^2O)_xSi$—K (group, $R^2$ is a ($C_1$ to $C_4$) alkyl group (particularly methyl or ethyl), $R^3$ is a ($C_1$ to $C_6$) alkyl group or an aryl group (particularly methyl), x is 1, 2, 3 (particularly 3).

In a further embodiment (for manufacture) of the polyether-modified organic compounds according to the present invention, at least one molecule fragment T of formula (PE-1) or formula (I) or formula (III) has at least one anionic group.

Molecule fragments T of formula (I) or formula (III) having at least one anionic group preferably refer, according to the present invention, to a molecule fragment having 1 to 5, by preference 3, 4, or 5 deprotonatable acid groups. The anionic groups or the deprotonatable acid groups of the aforesaid molecule fragments T of formula (I) or formula (III) are preferably chosen from a carboxyl group and/or sulfonic-acid group and/or phosphate or the respective salt forms thereof (in particular a carboxyl group and/or sulfonic-acid group or their respective salt forms, particularly preferably a carboxyl group or salt form thereof).

In a particularly preferred embodiment, the molecule fragment T of formula (I) or formula (III) contains at least 2, preferably 1 to 5, more preferably 2 to 5, in particular 2, 3, 4, or 5 carboxymethyl units. In a very particularly preferred embodiment, the aforesaid molecule fragment is an ethylenediaminetriacetate unit that is bound covalently, via one of its nitrogen atoms, to the connectivity K of formula (1) or formula (III).

In a preferred embodiment for manufacture of polyether-modified organic compounds according to the present invention, the molecule fragment T of formula (PE-1) or formula (I) or formula (III) is a silyl group of general formula (IV)

$$—CR^a_2—Si(OR^b)_r(R^c)_{3-r} \quad (IV),$$

such that $R^a$ is hydrogen or $C_{1-6}$ alkyl, $R^b$ is —$Si(R^d)_t(R^e)_{3-t}$, $R^c$ is ($C_1$ to $C_6$) alkyl, ($C_1$ to $C_6$) alkoxy or hydroxy, preferably ($C_1$ to $C_6$) alkoxy or hydroxy, $R^d$ is a negatively charged group, $R^e$ is ($C_1$ to $C_6$) alkyl, $C_{1-6}$ alkoxy or hydroxy, preferably ($C_1$ to $C_6$) alkoxy or hydroxy, r is a number from 1 to 3, preferably 1 t is a number from 1 to 3, preferably 1.

$R^d$ preferably is a unit having 1 to 5, preferably 3, 4, or 5 acid groups, particularly carboxylic acid groups.

Particularly preferably, $R^d$ in formula (IV) is a

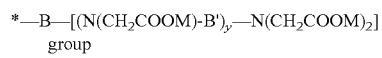

group such that

B is a ($C_1$ to $C_6$) alkylene residue, (preferably ethane-1,2-diyl, propane-1,2-diyl, propane-1,3-diyl, butane-1,2-diyl, butane-1,3-diyl, butane-1,4-diyl), B' is a ($C_1$ to $C_6$) alkylene residue, (preferably ethane-1,2-diyl, propane-1,2-diyl, propane-1,3-diyl, butane-1,2-diyl, butane-1,3-diyl, butane-1,4-diyl), M is mutually independently, a hydrogen atom or an equivalent of a mono- or polyvalent cation, y is 1 or 2 (preferably 1).

If the above group is present as an acid, the residue M signifies a hydrogen atom. In this case the —COOH fragments form a carboxyl group. If the above group is present in its salt form (carboxylate), M is an equivalent of a mono- or polyvalent cation. The mono- or polyvalent cation $M^{z+}$ having a charge number z of one or higher serves, solely for reasons of electroneutrality, to compensate for the single negative charge of the carboxylate present in the context of salt formation. The equivalent of the corresponding cation to be used is equal to 1/z. In the case of salt formation, the —COOM fragment is the group: —$COO^-$ 1/z ($M^{z+}$).

All cations that are physiologically acceptable are suitable in principle as mono- or polyvalent cations $M^{z+}$. These are, in particular, metal cations of the physiologically acceptable metals from groups Ia, Ib, IIa, IIb, IIIb, VIa, or VIII of the periodic table of the elements, ammonium ions, and cationic organic compounds having a quaternized nitrogen atom. The latter are formed, for example, by protonation of primary, secondary, or tertiary organic amines with an acid, for example with compounds of the above $R^d$ group in its acid form, or by permanent quaternization of the aforesaid organic amines. Examples of these cationic organic ammonium compounds are 2-ammonioethanol and 2-trimethylammonioethanol. M preferably denotes a hydrogen atom, an ammonium ion, an alkali metal ion, a half-equivalent of an alkaline-earth metal ion, or a half-equivalent of a zinc ion, particularly preferably a hydrogen atom, an ammonium ion, a sodium ion, a potassium ion, ½-calcium ion, ½-magnesium ion, or ½-zinc ion.

A very particularly preferred molecule fragment T of formula (PE-1) or formula (I) or formula (III) for manufacture of the polyether-modified organic compounds according to the present invention conforms to the general formula

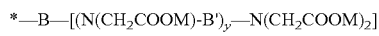

such that
B is a ($C_1$ to $C_6$) alkylene residue, (preferably ethane-1,2-diyl, propane-1,2-diyl, propane-1,3-diyl, butane-1,2-diyl, butane-1,3-diyl, butane-1,4-diyl),
B' is a ($C_1$ to $C_6$) alkylene residue, (preferably ethane-1,2-diyl, propane-1,2-diyl, propane-1,3-diyl, butane-1,2-diyl, butane-1,3-diyl, butane-1,4-diyl) or an N,N-bis($C_1$ to $C_6$) alkylene-N-carboxymethyl,
M is, mutually independently, a hydrogen atom or an equivalent of a mono- or polyvalent cation,
y is 1 or 2 (preferably 1).

The statements made previously (vide supra) apply to the residue M of the above formula.

Particularly preferred agents of this embodiment comprise polyether-modified organic compounds having at least one polyether having at least one molecule fragment T or T' of the aforesaid general formula *—B—[(N(CH$_2$COOM)-B')$_y$—N(CH$_2$COOM)$_2$].

Particularly preferred molecule fragments T of formula (PE-1) resp. formula (I) resp. formula (III) having the formula *—B—[(N(CH$_2$COOM)-B')$_y$—N(CH$_2$COOM)$_2$] are selected from at least one representative of the group that is constituted from 3-N-carboxylmethyl-N-(2'-N',N'-di(carboxymethylamino)ethyl)aminopropyl (B=propane-1,3-diyl, B'=ethane-1,2-diyl, y=1, M as above), 3-N-carboxylmethyl-N-(2'-N',N'-di(carboxymethylamino)ethyl)-N''-carboxymethylaminoethyl)aminopropyl (B=propane-1,3-diyl, B'=ethane-1,2-diyl, y=2, M as above). 3-N-Carboxylmethyl-N-(2'-N',N'-di(carboxymethylamino)ethyl)aminopropyl is very particularly preferred.

Very particularly preferred compounds for manufacturing the polyether-modified organic compounds according to the present invention are selected from at least one compound of formula (I-1c)—

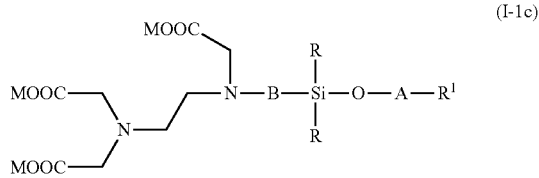

wherein
A is a polyoxyalkylene chain made up of ethylene oxide units or of ethylene oxide units and propylene oxide units, having a maximum proportion of 50 wt % propylene oxide units based on the weight of A,
B is a ($C_1$ to $C_6$) alkylene residue, (preferably ethane-1,2-diyl, propane-1,2-diyl, propane-1,3-diyl, butane-1,2-diyl, butane-1,3-diyl, butane-1,4-diyl),
B' is a ($C_1$ to $C_6$) alkylene residue, (preferably ethane-1,2-diyl, propane-1,2-diyl, propane-1,3-diyl, butane-1,2-diyl, butane-1,3-diyl, butane-1,4-diyl) or an N,N-bis($C_1$ to $C_6$) alkylene-N-carboxymethyl,
M is, mutually independently, a hydrogen atom or an equivalent of a mono- or polyvalent cation,
$R^1$ is an $R^3_{3-x}$—($R^2O$)$_x$—Si—K— group, wherein
$R^2$ and $R^3$, mutually independently, are a ($C_1$ to $C_4$) alkyl group (in particular ethyl or methyl),
x is a whole number 1, 2, or 3 (in particular 3),
K is a connectivity chosen from a covalent bond or from a molecule fragment having two free valences, and
R is, mutually independently, a ($C_1$ to $C_4$) alkyl group (in particular methyl or ethyl) or a ($C_2$ to $C_6$) alkoxy group (in particular methoxy or ethoxy).

As a compound of formula (III), this is preferably reacted with polyether polyols, in accordance with the method described above, to yield the polyether-modified organic compounds according to the present invention.

For the above-mentioned formula (I-1c), the preferred embodiments with regard to the aforementioned preferred features for A, B, B', M, $R^1$, and R apply mutatis mutandis.

Wettability with water of coatings achieved by way of agents according to the present invention is a sensitive indicator of their hydrophilicity or hydrophobicity. The contact angle of a water droplet on a planar substrate in air as the surrounding medium results from the surface energies of the coating and of the water, and from the interfacial energy between water and the coating in accordance with the Young equation. In the case of maximum hydrophilicity, the contact angle approaches 0°. In the case of maximum hydrophobicity, the contact angle approaches 180°. In practice, the advancing contact angle and the receding contact angle are often measured. Ideally, the difference between the two should equal zero; in reality, a difference does exist, also called the "contact angle hysteresis," which is attributed to surface roughness, inhomogeneities, and contaminants.

Coatings according to the present invention preferably possess a static water contact angle, measured with the sessile drop method (see Examples section for procedure), of up to 90°, preferably up to 70°, more preferably up to 55°, and even more preferably up to 45°. In many cases, however, water contact angles of 40° and below are also achieved. Very particularly preferably, agents according to the present invention contain polyethers of formula (I), so that after the treatment of keratin-containing fibers, particularly human hair, with the agent, the coating obtained exhibits a contact angle of from 20° to 60°.

Agents according to the present invention furthermore contain, besides the polyether-modified organic compounds according to the present invention, obligatorily at least one film-forming polymer and/or setting polymer. These polymers are different from the aforesaid polyether-modified organic compounds.

"Film-forming polymers" are those polymers that, upon drying, leave behind a continuous film on the skin, hair, or nails. Film-formers of this kind can be used in a very wide variety of cosmetic products such as face masks, make-up, hair setting agents, hair sprays, hair gels, hair waxes, hair therapies, shampoos, or nail polishes. Particularly preferred are those polymers having sufficient solubility in alcohol or in water/alcohol mixtures to be present in completely dissolved form in the agent. The film-forming polymers can be of synthetic or natural origin.

"Film-forming polymers" are furthermore those polymers that, when applied in a 0.01- to 20-wt % aqueous, alcoholic, or aqueous alcoholic solution, are capable of depositing a transparent polymer film on the hair.

Setting polymers contribute to the hold, and/or to building up the hair volume and hair fullness, of the overall hairstyle. These polymers are at the same time also film-forming polymers and are therefore generally typical substances for shape-imparting hair-treatment agents such as hair setting agents, hair foams, hair waxes, hair sprays. It is certainly possible for film formation to be localized, and for only a few fibers to be connected to one another.

The "curl retention" test or three-point bending test is often used as a test method for the setting effect of a polymer.

Preferred agents contain the film-forming and/or setting polymers in a quantity from 0.1 wt % to 20.0 wt %, particularly preferably from 0.2 wt % to 10.0 wt %, very particularly preferably from 0.5 wt % to 5.0 wt %, based on weight of the agent.

The agent according to the present invention preferably contains as a film-forming and/or setting polymer
at least one cationic film-forming and/or cationic setting polymer, and/or
at least one nonionic film-forming and/or nonionic setting polymer, and/or
at least one anionic film-forming and/or anionic setting polymer, and/or
at least one amphoteric film-forming and/or amphoteric setting polymer.

In a preferred embodiment, agents according to the present invention contain as a film-forming and/or setting polymer at least one cationic film-forming and/or cationic setting polymer.

Cationic film-forming and/or cationic setting polymers have at least one structural unit that contains at least one permanently cationized nitrogen atom. "Permanently" cationized nitrogen atoms refer to those nitrogen atoms that carry a positive charge and thereby form a quaternary ammonium compound. Quaternary ammonium compounds are usually produced by reaction of tertiary amines with alkylating agents such as methyl chloride, benzyl chloride, dimethyl sulfate, dodecyl bromide, but also ethylene oxide. Depending on the tertiary amine used, the following groups are known in particular: alkylammonium compounds, alkenylammonium compounds, imidazolinium compounds, and pyridinium compounds.

Preferred agents contain the cationic film-forming and/or cationic setting polymers in a quantity from 0.1 wt % to 20.0 wt %, particularly preferably from 0.2 wt % to 10.0 wt %, very particularly preferably from 0.5 wt % to 5.0 wt %, based on weight of the agent.

The cationic film-forming and/or cationic setting polymers can, according to the present invention, be chosen from cationic quaternized cellulose derivatives.

Those agents containing, in a cosmetically acceptable carrier,
a) polyether-modified organic compounds that are selected from at least one compound of the general formula (PE-1)

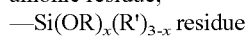     (PE-1)

wherein Q, K', A, K, T, and n are defined as described previously,
and
b) at least one cationic film-forming and/or cationic setting polymer chosen from cationic quaternized cellulose derivatives
are preferably suitable in the context of this embodiment.

Those agents containing, in a cosmetically acceptable carrier,
(a) polyether-modified organic compounds obtained by reacting
(i) organic compounds having at least three residues chosen from a hydroxy group and/or amino group (particularly from a hydroxy group, primary amino group, secondary amino group; particularly preferably hydroxy group(s)), with
(ii) at least 3 molar equivalents of at least one polyether of formula (I)

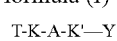     (I)

wherein
A is a polyoxyalkylene chain made up of ethylene oxide units or of ethylene oxide units and propylene oxide units, having a maximum proportion of 50 wt % propylene oxide units based on the weight of A,
K and K' are, mutually independently, a connectivity selected from a covalent bond or from a molecule fragment having two free valences,
T is a molecule fragment having at least one substituent chosen from
anionic residue,
—Si(OR)$_x$(R')$_{3-x}$ residue
wherein R and R' are, mutually independently, a (C$_1$ to C$_4$) alkyl group (in particular methyl or ethyl), and
x is 1, 2, or 3,
Y is a group reactive with respect to a hydroxy group or amino group,
and
(b) at least one cationic film-forming and/or cationic setting polymer chosen from cationic quaternized cellulose derivatives
are preferably suitable in the context of this embodiment.

Those agents containing, in a cosmetically acceptable carrier,
(a) polyether-modified organic compounds that are obtained by reacting
(i) organic polyether polyol compounds having
at least three polyoxyalkylene chains made up of ethylene oxide units or of ethylene oxide units and propylene oxide units, having a maximum proportion of 50 wt % propylene oxide units based on the weight of the polyoxyalkylene chain,
at least three hydroxy groups
with
(ii) at least 3 molar equivalents of at least one compound of formula (III)

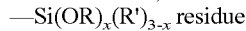     (III), wherein
Y is a group that is reactive with respect to OH, NH$_2$, NHR, NR$_2$,
K is a connectivity chosen from a covalent bond or from a molecule fragment having two free valences,
T is a molecule fragment having at least one substituent chosen from
anionic residue,
—Si(OR)$_x$(R')$_{3-x}$ residue
wherein R and R' are, mutually independently, a (C$_1$ to C$_4$) alkyl group (particularly methyl or ethyl), and
x is 1, 2, or 3.
and
(b) at least one cationic film-forming and/or cationic setting polymer chosen from cationic quaternized cellulose derivatives
are preferably suitable in the context of this embodiment.

Those cationic quaternized celluloses that carry more than one permanent cationic charge in a side chain turn out in general to be advantageous for purposes of the embodiment.

Among the cationic cellulose derivatives are those manufactured by reaction of hydroxyethyl cellulose with a dimethyldiallylammonium reactant (particularly dimethyldiallylammonium chloride), optionally in the presence of further reactants. Among these cationic celluloses, those having the INCI name Polyquaternium-4, marketed, for example, under the designations Celquat® H 100, Celquat® L 200 by the National Starch company, are in turn particularly suitable.

Those agents containing, in a cosmetically acceptable carrier, a) polyether-modified organic compounds that are selected from at least one compound of the general formula (PE-1)

[Q—]—(—K'-A-K-T)$_n$ (PE-1)

wherein Q, K', A, K, T, and n are defined as described previously, and b) at least one additional cationic film-forming and/or cationic setting polymer chosen from cationic quaternized cellulose derivatives manufactured by reaction of hydroxyethyl cellulose with a dimethyldiallylammonium reactant (particularly dimethyldiallylammonium chloride), optionally in the presence of further reactants, therefore emerge as suitable in the context of this embodiment.

Those agents containing, in a cosmetically acceptable carrier, (a) polyether-modified organic compounds that are obtained by reacting
  (i) organic compounds containing at least three residues chosen from a hydroxy group and/or amino group (particularly from a hydroxy group, primary amino group, secondary amino group; particularly preferably hydroxy group(s)) with
  (ii) at least 3 molar equivalents of at least one polyether of formula (I)

T-K-A-K'—Y (I)

wherein
  A is a polyoxyalkylene chain made up of ethylene oxide units or of ethylene oxide units and propylene oxide units, having a maximum proportion of 50 wt % propylene oxide units based on the weight of A,
  K and K' are, mutually independently, a connectivity selected from a covalent bond or from a molecule fragment having two free valences,
  T is a molecule fragment having at least one substituent chosen from
    anionic residue,
    —Si(OR)$_x$(R')$_{3-x}$ residue
      wherein R and R' are, mutually independently, a (C$_1$ to C$_4$) alkyl group (particularly methyl or ethyl), and
      x is 1, 2, or 3,
  Y is a group reactive with respect to a hydroxy group or amino group, and (b) at least one additional cationic film-forming and/or cationic setting polymer chosen from cationic quaternized cellulose derivatives manufactured by reaction of hydroxyethyl cellulose with a dimethyldiallylammonium reactant (particularly dimethyldiallylammonium chloride), optionally in the presence of further reactants, are preferable suitable in the context of this embodiment.

Those agents containing, in a cosmetically acceptable carrier, (a) polyether-modified organic compounds that are obtained by reacting
  (i) organic polyether polyol compounds encompassing at least three polyoxyalkylene chains made up of ethylene oxide units or of ethylene oxide units and propylene oxide units, having a maximum proportion of 50 wt % propylene oxide units based on the weight of the polyoxyalkylene chain,
  at least three hydroxy groups
  with
  (ii) at least 3 molar equivalents of at least one compound of formula (III)

Y—K-T (III)

wherein
  Y is a group that is reactive with respect to OH, NH$_2$, NHR, NR$_2$,
  K is a connectivity chosen from a covalent bond or from a molecule fragment having two free valences,
  T is a molecule fragment having at least one substituent chosen from
    anionic residue,
    —Si(OR)$_x$(R')$_{3-x}$ residue
      wherein R and R' are, mutually independently, a (C$_1$ to C$_4$) alkyl group (particularly methyl or ethyl), and
      x is 1, 2, or 3 and (b) at least one additional cationic film-forming and/or cationic setting polymer chosen from cationic quaternized cellulose derivatives manufactured by reaction of hydroxyethyl cellulose with a dimethyldiallylammonium reactant (particularly dimethyldiallylammonium chloride), optionally in the presence of further reactants therefore emerge as suitable in the context of this embodiment.

In the context of these aforementioned embodiments, the previously recited preferred embodiments of the polyether of formula (I) are suitable (vide supra). Similarly, all the previously recited preferred quantitative indications with regard to components (a) and (b) of the agent according to the present invention are considered well-suited for these embodiments as well, mutatis mutandis.

Also suitable are those cationic film-forming and/or cationic setting polymers (b) that encompass at least one structural unit of formula (M-I) and at least one structural unit of formula (M-VI) and optionally at least one structural unit of formula (M-V),

(I)

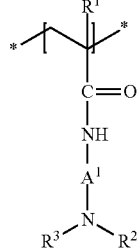

(V)

-continued

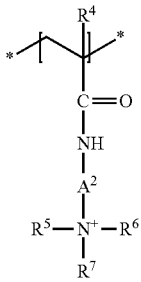
(VI)

wherein

R¹ and R4, mutually independently, are a hydrogen atom or a methyl group,

A¹ and A², mutually independently, are an ethane-1,2-diyl, propane-1,3-diyl, or butane-1,4-diyl group, R², R³, R⁵, and R⁶, mutually independently, are a ($C_1$ to $C_4$) alkyl group, R⁷ is a ($C_8$ to $C_{30}$) alkyl group.

All possible physiologically acceptable anions, for example chloride, bromide, hydrogen sulfate, methyl sulfate, ethyl sulfate, tetrafluoroborate, phosphate, hydrogen phosphate, dihydrogen phosphate, or p-toluenesulfonate, triflate, serve to compensate for the positive charge of monomer (M-VI).

Those agents containing, in a cosmetically acceptable carrier, a) polyether-modified organic compounds that are selected from at least one compound of the general formula (PE-1)

(PE-1)

where Q, K', A, K, T, and n are defined as described previously, and b) at least one additional cationic film-forming and/or cationic setting polymer having at least one structural unit of formula (M-I) and at least one structural unit of formula (M-VI) and optionally at least one structural unit of formula (M-V),

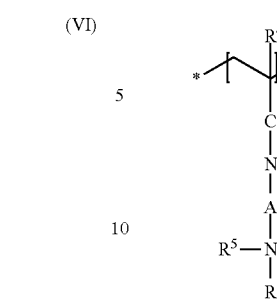
(M-I)

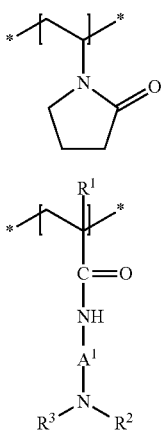
(M-V)

-continued

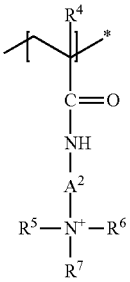
(M-VI)

wherein

R¹ and R⁴, mutually independently, are a hydrogen atom or a methyl group,

A¹ and A², mutually independently, are an ethane-1,2-diyl, propane-1,3-diyl, or butane-1,4-diyl group, R², R³, R⁵, and R⁶, mutually independently, are a ($C_1$ to $C_4$) alkyl group, R⁷ is a ($C_8$ to $C_{30}$) alkyl group, are considered preferably suitable for purposes of the present invention.

Those agents containing, in a cosmetically acceptable carrier, (a) polyether-modified organic compounds that are obtained by reacting (i) organic compounds containing at least three residues chosen from a hydroxy group and/or amino group (particularly from a hydroxy group, primary amino group, secondary amino group; particularly preferably hydroxy group(s)), with (ii) at least 3 molar equivalents of at least one polyether of formula (I)

(I)

wherein

A is a polyoxyalkylene chain made up of ethylene oxide units or of ethylene oxide units and propylene oxide units, having a maximum proportion of 50 wt % propylene oxide units based on the weight of A, K and K' are, mutually independently, a connectivity chosen from a covalent bond or from a molecule fragment having two free valences, T is a molecule fragment having at least one substituent chosen from anionic residue, —Si(OR)$_x$(R')$_{3-x}$ residue wherein R and R' are, mutually independently, a ($C_1$ to $C_4$) alkyl group (particularly methyl or ethyl), x is 1, 2, or 3, Y is a group reactive with respect to a hydroxy group or amino group, and (b) at least one additional cationic film-forming and/or cationic setting polymer having at least one structural unit of formula (M-I) and at least one structural unit of formula (M-VI) and optionally at least one structural unit of formula (M-V),

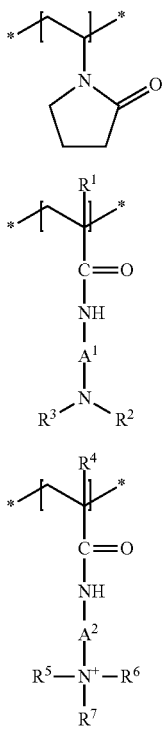

(I)

(V)

(VI)

wherein
$R^1$ and $R^4$, mutually independently, are a hydrogen atom or a methyl group,
$A^1$ and $A^2$, mutually independently, are an ethane-1,2-diyl, propane-1,3-diyl, or butane-1,4-diyl group,
$R^2$, $R^3$, $R^5$, and $R^6$, mutually independently, are a ($C_1$ to $C_4$) alkyl group,
$R^7$ is a ($C_8$ to $C_{30}$) alkyl group,
are preferably suitable for purposes of the present invention.

Those agents containing, in a cosmetically acceptable carrier,
(a) polyether-modified organic compounds obtained by reacting
 (i) organic polyether polyol compounds having
  at least three polyoxyalkylene chains made up of ethylene oxide units or of ethylene oxide units and propylene oxide units, having a maximum proportion of 50 wt % propylene oxide units based on the weight of the polyoxyalkylene chain,
  at least three hydroxy groups
with
 (ii) at least 3 molar equivalents of at least one compound of formula (III)

Y—K—T     (III)

wherein
Y is a group that is reactive with respect to OH, $NH_2$, NHR, $NR_2$,
K is a connectivity chosen from a covalent bond or from a molecule fragment having two free valences,
T is a molecule fragment having at least one substituent chosen from
 anionic residue,
 —$Si(OR)_x(R')_{3-x}$ residue
  wherein R and R' are, mutually independently, a ($C_1$ to $C_4$) alkyl group (particularly methyl or ethyl),
  x is 1, 2, or 3, and
(b) at least one additional cationic film-forming and/or cationic setting polymer having at least one structural unit of formula (M-I) and at least one structural unit of formula (M-VI) and optionally at least one structural unit of formula (M-V),

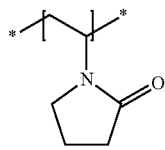

(I)

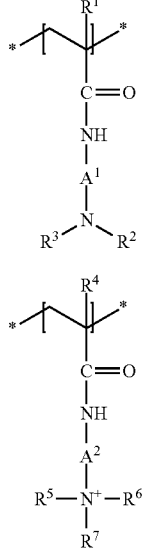

(V)

(VI)

wherein
$R^1$ and $R^4$, mutually independently, are a hydrogen atom or a methyl group,
$A^1$ and $A^2$, mutually independently, are an ethane-1,2-diyl, propane-1,3-diyl, or butane-1,4-diyl group,
$R^2$, $R^3$, $R^5$, and $R^6$, mutually independently, are a ($C_1$ to $C_4$) alkyl group,
$R^7$ is a ($C_8$ to $C_{30}$) alkyl group,
are considered preferably suitable for purposes of the present invention.

The statements made above are applicable respectively with regard to compensation for the positive charge of the monomer (M-VI).

Suitable compounds are obtainable commercially, for example, as
 copolymers of dimethylaminoethyl methacrylate, quaternized with diethyl sulfate, with vinylpyrrolidone, having the INCI name Polyquaternium-11, under the designations Gafquat® 440, Gafquat® 734, Gafquat® 755 (each ISP company) and Luviquat PQ 11 PN (BASF SE),
 copolymers of methacryloylaminopropyllauryldimethylammonium chloride with vinylpyrrolidone and dimethylaminopropyl methacrylamide, having the INCI name Polyquaternium-55, under the commercial names Styleze® W-10, Styleze® W-20 (ISP company).

In the context of these aforementioned embodiments, the previously recited preferred embodiments of the polyether of formula (I) are preferably suitable (vide supra).

Similarly, all the previously recited preferred quantitative indications with regard to components (a) and (b) of the agent according to the present invention are considered preferred for these embodiments as well, mutatis mutandis.

Also serving as film-forming and/or setting polymers, selected from cationic polymers that contain at least one structural unit that comprises a permanently cationized nitrogen atom, that are usable particularly preferably for purposes of the invention are those cationic film-forming and/or cationic setting copolymers (b) that contain at least one structural element of formula (M1)

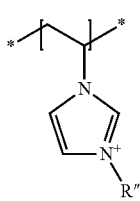

(M1)

wherein
R" is a ($C_1$ to $C_4$) alkyl group, particularly a methyl group, and which additionally comprise at least one further cationic and/or nonionic structural element.

Those agents containing, in a cosmetically acceptable carrier,
a) polyether-modified organic compounds chosen from at least one compound of the general formula (PE-1)

[Q—(—K'-A-K-T)]$_n$  (PE-1)

where Q, K', A, K, T, and n are defined as described previously,
and
b) at least one additional cationic film-forming and/or cationic setting polymer that contains, as at least one structural unit having a permanently cationized nitrogen atom, at least one structural element of formula (M1)

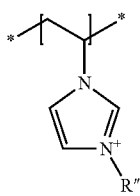

(M1)

wherein
R" is a ($C_1$ to $C_4$) alkyl group, particularly a methyl group, and which additionally comprises at least one further cationic and/or nonionic structural element,
are therefore considered particularly preferred for purposes of the present invention.

All possible physiologically acceptable anions, for example, chloride, bromide, hydrogen sulfate, methyl sulfate, ethyl sulfate, tetrafluoroborate, phosphate, hydrogen phosphate, dihydrogen phosphate, or p-toluenesulfonate, triflate, serve to compensate for the positive charge of component (b).

Also considered very particularly preferred in the context of this embodiment are, in particular, those cosmetic agents that contain, in a cosmetically acceptable carrier,
(a) polyether-modified organic compounds obtained by reacting
   (i) organic polyether polyol compounds having
      at least three polyoxyalkylene chains made up of ethylene oxide units or of ethylene oxide units and propylene oxide units, having a maximum proportion of 50 wt % propylene oxide units based on the weight of the polyoxyalkylene chain,
      at least three hydroxy groups
   with
   (ii) at least 3 molar equivalents of at least one compound of formula (III)

Y—K-T  (III)

in which
   Y is a group that is reactive with respect to OH, $NH_2$, NHR, $NR_2$,
   K is a connectivity selected from a covalent bond or from a molecule fragment having two free valences,
   T is a molecule fragment encompassing at least one substituent selected from
      anionic residue,
      —$Si(OR)_x(R')_{3-x}$ residue
         wherein R and R' are, mutually independently, a ($C_1$ to $C_4$) alkyl group (particularly methyl or ethyl),
         x is 1, 2, or 3
and
(b) at least one cationic film-forming and/or cationic setting polymer having at least one structural element of formula (M1)

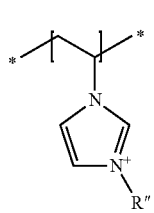

(M1)

wherein
R" is a ($C_1$ to $C_4$) alkyl group, particularly a methyl group, and which additionally comprises at least one further cationic and/or nonionic structural element.

Those cosmetic agents containing, in a cosmetically acceptable carrier,
(a) polyether-modified organic compounds that are obtained by reacting
   (i) organic compounds containing at least three residues chosen from a hydroxy group and/or amino group (particularly from a hydroxy group, primary amino group, secondary amino group; particularly preferably hydroxy group(s)), with
   (ii) at least 3 molar equivalents of at least one polyether of formula (I)

T-K-A-K'—Y  (I)

wherein
   A is a polyoxyalkylene chain made up of ethylene oxide units or of ethylene oxide units and propylene oxide units, having a maximum proportion of 50 wt % propylene oxide units based on the weight of A,
   K and K' are, mutually independently, a connectivity chosen from a covalent bond or from a molecule fragment having two free valences,
   T is a molecule fragment having at least one substituent chosen from anionic residue, —Si(OR)$_x$(R')$_{3-x}$ residue
  wherein R and R' are, mutually independently, a (C$_1$ to C$_4$) alkyl group (particularly methyl or ethyl),
  x is 1, 2, or 3,
Y is a group reactive with respect to a hydroxy group or amino group, and (b) at least one cationic film-forming and/or cationic setting polymer having at least one structural element of formula (M1)

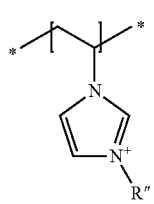
(M1)

wherein
R" is a (C$_1$ to C$_4$) alkyl group, particularly a methyl group, and which additionally comprises at least one further cationic and/or nonionic structural element, are preferably suitable in the context of this embodiment.

The statements made above are applicable with regard to compensation for the positive polymer charge of component (b).

Preferably the agent according to the present invention contains, besides the polyether of formula (I), as a cationic film-forming and/or cationic setting polymer (b) of this embodiment, at least one copolymer (b1) that, besides at least one structural element of formula (M1), additionally has a structural element of formula (M-I)

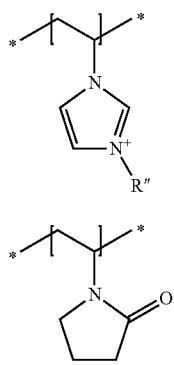
(M1)

(M-I)

wherein
R" is a (C$_1$ to C$_4$) alkyl group, particularly a methyl group.

All possible physiologically acceptable anions (e.g., chloride, bromide, hydrogen sulfate, methyl sulfate, ethyl sulfate, tetrafluoroborate, phosphate, hydrogen phosphate, dihydrogen phosphate, or p-toluenesulfonate, triflate) serve to compensate for the positive polymer charge of copolymers (b1).

Very particularly preferred cationic film-forming and/or cationic setting polymers constituting copolymers (b1) contain 10 to 30 mol %, preferably 15 to 25 mol %, and in particular 20 mol % structural units according to formula (M1), and 70 to 90 mol %, preferably 75 to 85 mol %, and in particular 80 mol % structural units according to formula (M-I).

It is particularly preferred in this context if copolymers (b1) contain, besides polymer units that result from incorporation of the aforesaid structural units according to formulas (M1) and (M-I) into the copolymer, a maximum of 5 wt %, preferably a maximum of 1 wt %, polymer units based on the incorporation of other monomers. Copolymers (b1) are preferably constructed exclusively from structural units of formula (M1), wherein R"=methyl, and (M-I), and can be described by the general formula (Poly1)

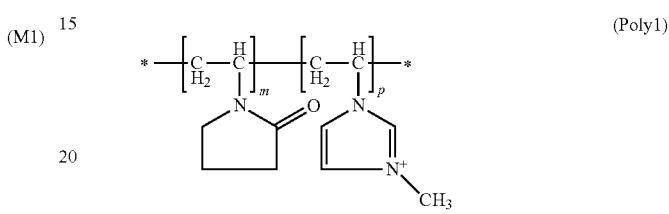
(Poly1)

wherein m and p each vary depending on the molar mass of the polymer and are not intended to signify that these are block copolymers. Structural units of formula (M1) and formula (M-I) can instead be present in statistically distributed fashion in the molecule.

If a chloride ion is used to compensate for the positive charge of the polymer of formula (Poly1), these N-methylvinylimidazole/vinylpyrrolidone copolymers are then according to INCI nomenclature referred to as Polyquaternium-16 and are obtainable, for example, from BASF under the trade names Luviquat® Style, Luviquat® FC 370, Luviquat® FC 550, Luviquat® FC 905, and Luviquat® HM 552.

If a methosulfate is used to compensate for the positive charge of the polymer of formula (Poly1), these N-methylvinylimidazole/vinylpyrrolidone copolymers are then according to INCI nomenclature referred to as Polyquaternium-44 and are obtainable e.g. from BASF under the trade names Luviquat® UltraCare.

Particularly preferred agents according to the present invention contain a copolymer (b1), particularly of formula (Poly1), having molar masses within a specific range. Agents according to the present invention wherein copolymer (b1) has a molar mass from 50 to 400 kDa, by preference from 100 to 300 kDa, more preferably from 150 to 250 kDa, and in particular from 190 to 210 kDa, are preferred here.

In addition to or instead of copolymer(s) (b1), agents according to the present invention can also contain copolymers (b2) that, proceeding from copolymer (b1), contain structural units of formula (M-II) as additional structural units:

(M-II)

Further particularly preferred agents according to the present invention therefore contain, as a cationic film-forming and/or cationic setting polymer (b), at least one copolymer (b2) having at least one structural unit according to formula (M1-a), at least one further structural unit according to formula (M-I), and at least one further structural unit according to formula (M-II)—

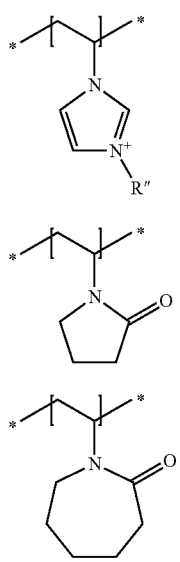

(M1-a)

(M-I)

(M-II)

Here as well, it is particularly preferred if copolymers (b2) contain, besides polymer units resulting from the incorporation of the aforesaid structural units according to formulas (M1-a), (M-I), and (M-II) into the copolymer, a maximum of 5 wt %, preferably a maximum of 1 wt %, polymer units based on the incorporation of other monomers. Copolymers (b2) are preferably constructed exclusively from structural units of formulas (M1-a), (M-I), and (M-II), and can be described by the general formula (Poly2)

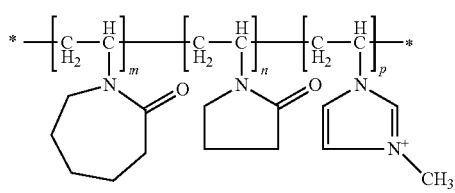

(Poly2)

wherein m, n and p each vary depending on the molar mass of the polymer and are not intended to signify that these are block copolymers. Structural units of the aforesaid formulas can instead be present in statistically distributed fashion in the molecule.

All possible physiologically acceptable anions (e.g., chloride, bromide, hydrogen sulfate, methyl sulfate, ethyl sulfate, tetrafluoroborate, phosphate, hydrogen phosphate, dihydrogen phosphate, or p-toluenesulfonate triflate) serve to compensate for the positive polymer charge of component (b2).

If a methosulfate is used to compensate for the positive charge of the polymer of formula (Poly2), these N-methylvinylimidazole/vinylpyrrolidone/vinylcaprolactam copolymers are then referred to according to INCI nomenclature as Polyquaternium-46 and are obtainable, for example, from BASF under the trade name Luviquat® Hold.

Very particularly preferred copolymers (b2) contain 1 to 20 mol %, preferably 5 to 15 mol %, and in particular 10 mol % structural units according to formula (M-1a), and 30 to 50 mol %, preferably 35 to 45 mol %, and in particular 40 mol % structural units according to formula (I), and 40 to 60 mol %, preferably 45 to 55 mol %, and in particular 60 mol % structural units according to formula (M-II).

Particularly preferred agents according to the present invention contain a copolymer (b2) having molar masses within a specific range. Agents according to the present invention wherein copolymer (b2) has a molar mass from 100 to 1000 kDa, preferably from 250 to 900 kDa, more preferably from 500 to 850 kDa, and in particular from 650 to 710 kDa, are preferred here.

In addition to or instead of copolymer(s) (b1) and/or (b2), agents according to the present invention can also contain as a cationic film-forming and/or cationic setting polymer copolymers (b3) having as structural units structural units of formulas (M1-a) and (I), as well as further structural units from vinylimidazole units and further structural units from acrylamide and/or methacrylamide units.

Further particularly preferred agents contain, as a cationic film-forming and/or cationic setting polymer, at least one copolymer (b3) having at least one structural unit according to formula (M-1a), at least one structural unit according to formula (M-I), at least one structural unit according to formula (M-VII), and at least one structural unit according to formula (M-VIII)

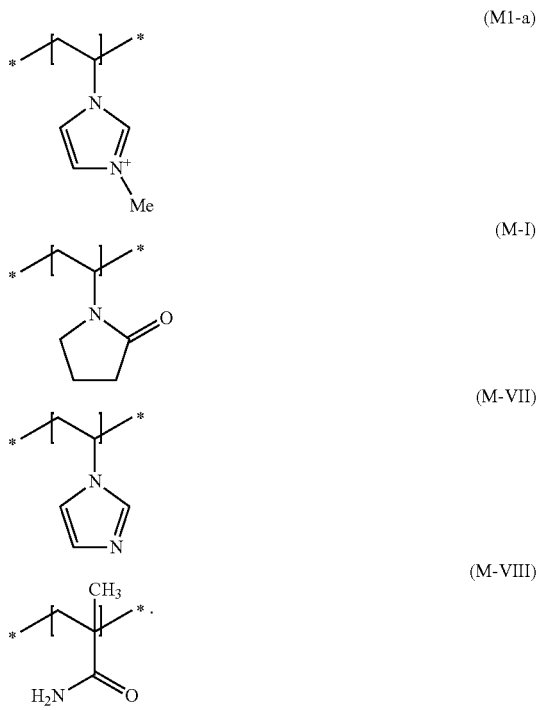

(M1-a)

(M-I)

(M-VII)

(M-VIII)

Here as well, it is particularly preferred if copolymers (b3) contain, besides polymer units that result from incorporation of the aforesaid structural units according to formulas (M1-a), (M-I), (M-VII), and (M-VIII) into the copolymer, a maximum of 5 wt %, preferably a maximum of 1 wt %, polymer units based on the incorporation of other monomers. Copolymers (b3) are preferably constructed exclusively from structural units of formulas (M1-a), (M-I), (M-VII), and (M-VIII) and can be described by the general formula (Poly3)

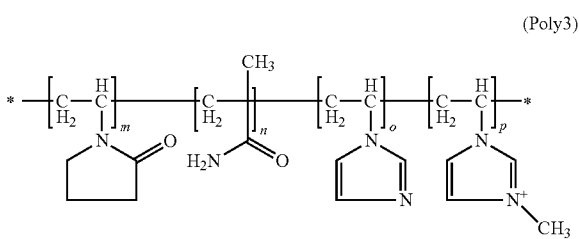

(Poly3)

wherein m, n, o and p each vary depending on the molar mass of the polymer and are not intended to signify that these are block copolymers. Structural units of formulas (M1-a), (M-I), (M-VII), and (M-VIII) can instead be present in statistically distributed fashion in the molecule.

All possible physiologically acceptable anions, for example chloride, bromide, hydrogen sulfate, methyl sulfate, ethyl sulfate, tetrafluoroborate, phosphate, hydrogen phosphate, dihydrogen phosphate, or p-toluenesulfonate, triflate, serve to compensate for the positive polymer charge of component (b2).

If a methosulfate is used to compensate for the positive charge of the polymer of formula (Poly3), these N-methylvinylimidazole/vinylpyrrolidone/vinylimidazole/methacrylamide copolymers are according to INCI nomenclature referred to as Polyquaternium-68 and are obtainable, for example, from BASF under the trade name Luviquat® Supreme.

Very particularly preferred copolymers (b3) contain 1 to 12 mol %, preferably 3 to 9 mol %, and in particular 6 mol % structural units according to formula (M-1a), and 45 to 65 mol %, preferably 50 to 60 mol %, and in particular 55 mol % structural units according to formula (M-I), and 1 to 20 mol %, preferably 5 to 15 mol %, and in particular 10 mol % structural units according to formula (M-VII), and 20 to 40 mol %, preferably 25 to 35 mol %, and in particular 29 mol % structural units according to formula (M-VIII).

Particularly preferred agents contain a copolymer (b3) having molar masses within a specific range. Agents according to the present invention wherein copolymer (b3) has a molar mass from 100 to 500 kDa, preferably 150 to 400 kDa, more preferably 250 to 350 kDa, and in particular 290 to 310 kDa, are preferred here.

Among the additional cationic film-forming and/or setting polymers selected from the cationic polymers (b) having at least one structural element of the above formula (M1), those considered preferred are:

vinylpyrrolidone/1-vinyl-3-methyl-1H-imidazolium chloride copolymers (such as, for example, the one having the INCI name Polyquaternium-16 under the commercial designations Luviquat® Style, Luviquat® FC 370, Luviquat® FC 550, Luviquat® FC 905, and Luviquat® HM 552 (BASF SE)), vinylpyrrolidone/1-vinyl-3-methyl-1H-imidazolium methyl sulfate copolymers (such as, for example, the one having the INCI name Polyquaternium-44 under the commercial designations Luviquat® Care (BASF SE)), vinylpyrrolidone/vinylcaprolactam/1-vinyl-3-methyl-1H-imidazolium terpolymers (such as, for example, the one having the INCI name Polyquaternium-46 under the commercial designations Luviquat® Care or Luviquat® Hold (BASF SE)), vinylpyrrolidone/methacrylamide/vinylimidazole/1-vinyl-3-methyl-1H-imidazolium methyl sulfate copolymers (such as, for example, the one having the INCI name Polyquaternium-68 under the commercial designations Luviquat® Supreme (BASF SE)), as well as mixtures of said polymers.

In the context of these embodiments, the previously recited preferred embodiments of the polyether of formula (I) are preferably suitable (vide supra).

Similarly, all the previously recited preferred quantitative indications with regard to components (a) and (b) of the agent according to the present invention are considered preferred for these embodiments as well, mutatis mutandis.

In the context of a preferred embodiment, the agents according to the present invention contain, as a film-forming and/or setting polymer, at least one nonionic film-forming and/or nonionic setting polymer.

A "nonionic polymer" is understood according to the present invention as a polymer that, in a protic solvent under standard conditions, carries substantially no structural units having permanently cationic or anionic groups that must be compensated for by counterions to maintain electroneutrality. "Cationic" groups include, for example, quaternized ammonium groups but not protonated amines. "Anionic" groups include, for example, carboxyl and sulfonic-acid groups.

The nonionic film-forming and/or nonionic setting polymers are contained in the agent according to the present invention preferably in a quantity from 0.1 wt % to 20.0 wt %, particularly preferably from 0.2 wt % to 15.0 wt %, very particularly preferably from 0.5 wt % to 10.0 wt %, based in each case on the weight of the agent according to the present invention.

The nonionic film-forming and/or nonionic setting polymers are in turn preferably selected from at least one polymer from homopolymers and nonionic copolymers of N-vinylpyrrolidone, nonionic copolymers of isobutene.

Suitable polyvinylpyrrolidones include commercial products such as Luviskol® K 90 or Luviskol® K 85 of the BASF SE Company.

Suitable polyvinyl alcohols are marketed, for example, under the commercial designations Elvanol® by Du Pont, or Vinol® 523/540 by the Air Products Company.

Suitable polyvinyl acetate is marketed, for example, as an emulsion under the trade name Vinac® by the Air Products Company.

Agents that contain, as a nonionic film-forming and/or nonionic setting polymer, at least one polymer selected from the group that is constituted from polyvinylpyrrolidone, copolymers of N-vinylpyrrolidone and vinyl esters of carboxylic acids having 2 to 18 carbon atoms, in particular of N-vinylpyrrolidone and vinyl acetate, copolymers of N-vinylpyrrolidone and N-vinylimidazole and methacrylamide, copolymers of N-vinylpyrrolidone and N-vinylimidazole and acrylamide, copolymers of N-vinylpyrrolidone with N,N-di($C_1$ to $C_4$) alkylamino-($C_2$ to $C_4$) alkylacrylamide, copolymers of N-vinylpyrrolidone with N,N-di($C_1$ to $C_4$) alkylamino-($C_2$ to $C_4$) alkylacrylamide, are very particularly preferred according to the present invention.

Those agents that contain, in a cosmetically acceptable carrier, (a) polyether-modified organic compounds chosen from at least one compound of general formula (PE-1)

$$[Q\text{—}(\text{—K'-A-K-T})_n] \qquad (PE-1)$$

where Q, K', A, K, T, and n are defined as described previously,
and
(b) polyvinylpyrrolidone
are furthermore considered in particular to be very particularly preferred in the context of this embodiment.

Those cosmetic agents containing, in a cosmetically acceptable carrier,
(a) polyether-modified organic compounds obtained by reacting
   (i) organic compounds containing at least three residues chosen from a hydroxy group and/or amino group (particularly from a hydroxy group, primary amino group, or secondary amino group; particularly preferably hydroxy group(s)), with
   (ii) at least 3 molar equivalents of at least one polyether of formula (I)

T-K-A-K'—Y    (I)

wherein
   A is a polyoxyalkylene chain made up of ethylene oxide units or of ethylene oxide units and propylene oxide units, having a maximum proportion of 50 wt % propylene oxide units based on the weight of A,
   K and K' are, mutually independently, a connectivity chosen from a covalent bond or from a molecule fragment having two free valences,
   T is a molecule fragment having at least one substituent chosen from
      anionic residue,
      —Si(OR)$_x$(R')$_{3-x}$ residue
         wherein R and R' are, mutually independently, a ($C_1$ to $C_4$) alkyl group (particularly methyl or ethyl),
         x is 1, 2, or 3,
   Y is a group reactive with respect to a hydroxy group or amino group,
and
(b) polyvinylpyrrolidone
are preferably suitable in the context of this embodiment.

Those cosmetic agents containing, in a cosmetically acceptable carrier,
(a) polyether-modified organic compounds that are obtained by reacting
   (i) organic polyether polyol compounds having
      at least three polyoxyalkylene chains made up of ethylene oxide units or of ethylene oxide units and propylene oxide units, having a maximum proportion of 50 wt % propylene oxide units based on the weight of the polyoxyalkylene chain,
      at least three hydroxy groups
   with
   (ii) at least 3 molar equivalents of at least one compound of formula (III)

Y—K-T    (III)

wherein
   Y is a group that is reactive with respect to OH, NH$_2$, NHR, NR$_2$,
   K is a connectivity chosen from a covalent bond or from a molecule fragment having two free valences,
   T is a molecule fragment having at least one substituent chosen from
      anionic residue,
      —Si(OR)$_x$(R')$_{3-x}$ residue
         wherein R and R' are, mutually independently, a ($C_1$ to $C_4$) alkyl group (particularly methyl or ethyl),
         x is 1, 2, or 3
and
(b) polyvinylpyrrolidone
are furthermore considered in particular to be very particularly preferred in the context of this embodiment.

Those cosmetic agents containing, in a cosmetically acceptable carrier,
(a) polyether-modified organic compounds chosen from at least one compound of general formula (PE-1)

[Q—(—K'-A-K-T)$_n$    (PEA-1)

where Q, K', A, K, T, and n are defined as described previously,
and
(b) at least a copolymer manufactured from the monomers N-vinylpyrrolidone and vinyl acetate (particularly from no further monomers)
are furthermore considered in particular to be very particularly preferred in the context of this embodiment.

Those cosmetic agents containing, in a cosmetically acceptable carrier,
(a) polyether-modified organic compounds that are obtained by reacting
   (i) organic compounds containing at least three residues selected from a hydroxy group and/or amino group (in particular: from a hydroxy group, primary amino group, secondary amino group; particularly preferably hydroxy group(s)), with
   (ii) at least 3 molar equivalents of at least one polyether of formula (I)

T-K-A-K'—Y    (I)

wherein
   A is a polyoxyalkylene chain made up of ethylene oxide units or of ethylene oxide units and propylene oxide units, having a maximum proportion of 50 wt % propylene oxide units based on the weight of A,
   K and K' are, mutually independently, a connectivity chosen from a covalent bond or from a molecule fragment having two free valences,
   T is a molecule fragment having at least one substituent chosen from
      anionic residue,
      —Si(OR)$_x$(R')$_{3-x}$ residue
         wherein R and R' are, mutually independently, a ($C_1$ to $C_4$) alkyl group (particularly methyl or ethyl),
         x is 1, 2, or 3,
   Y is a group reactive with respect to a hydroxy group or amino group,
and
(b) at least a copolymer manufactured from the monomers N-vinylpyrrolidone and vinyl acetate (in particular, from no further monomers)
are very particularly preferably suitable in the context of this embodiment.

Those cosmetic agents containing, in a cosmetically acceptable carrier,
(a) polyether-modified organic compounds that are obtained by reacting
   (i) organic polyether polyol compounds encompassing
      at least three polyoxyalkylene chains made up of ethylene oxide units or of ethylene oxide units and propylene oxide units, having a maximum proportion of 50 wt % propylene oxide units based on the weight of the polyoxyalkylene chain, at least three hydroxy groups with (ii) at least 3 molar equivalents of at least one compound of formula (III)

$$Y\text{—}K\text{-}T \tag{III}$$

wherein

Y is a group that is reactive with respect to OH, $NH_2$, NHR, $NR_2$,

K is a connectivity chosen from a covalent bond or from a molecule fragment having two free valences, T is a molecule fragment having at least one substituent chosen from anionic residue, $—Si(OR)_x(R')_{3-x}$ residue wherein R and R' are, mutually independently, a ($C_1$ to $C_4$) alkyl group (particularly methyl or ethyl), x is 1, 2, or 3 and (b) at least a copolymer manufactured from the monomers N-vinylpyrrolidone and vinyl acetate (in particular, from no further monomers)

are furthermore considered in particular to be very particularly preferred in the context of this embodiment.

It is preferred in turn if the molar ratio of the structural units of the polymer contained from the N-vinylpyrrolidone monomer to the structural units of the polymer contained from the vinyl acetate monomer is in the range from 20:80 to 80:20, in particular from 30:70 to 60:40.

Suitable copolymerizates of vinylpyrrolidone and vinyl acetate are obtainable, for example, under the trademarks Luviskol® VA 37, Luviskol® VA 55, Luviskol® VA 64, and Luviskol® VA 73 from the BASF SE Company.

Further preferred agents according to the present invention are characterized in that they contain, as a nonionic film-forming and/or nonionic setting polymer, at least one copolymer (n1) that contains at least one structural unit according to formula (M-I), at least one further structural unit according to formula (M-VII), and at least one further structural unit according to formula (M-VIII)

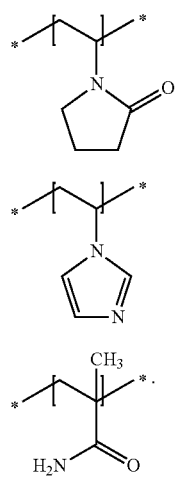

Here as well, it is particularly preferred if these copolymers contain, besides polymer units that result from incorporation of the aforesaid structural units according to formulas (M1-a), (I), (VII), and (VIII) into the copolymer, a maximum of 5 wt %, by preference a maximum of 1 wt %, polymer units that are based on the incorporation of other monomers. Copolymers (n1) are by preference constructed exclusively from structural units of formulas (M1-a), (I), (VII), and (VIII) and can be described by the general formula (Poly4)

Those agents that contain, in a cosmetically acceptable carrier, (a) polyether-modified organic compounds chosen from at least one compound of general formula (PE-1)

$$[Q\text{—}(\text{—}K'\text{-}A\text{-}K\text{-}T)_n \tag{PE-1}$$

where Q, K', A, K, T, and n are defined as described previously, and (b) at least one nonionic film-forming and/or nonionic setting polymer encompassing at least one structural unit according to formula (M-I), at least one further structural unit according to formula (M-VII), and at least one further structural unit according to formula (M-VIII)

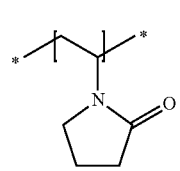

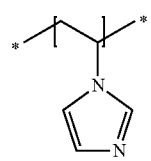

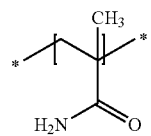

are furthermore considered in particular to be very particularly preferred in the context of this embodiment.

Those cosmetic agents containing, in a cosmetically acceptable carrier, (a) polyether-modified organic compounds obtained by reacting (i) organic compounds containing at least three residues chosen from a hydroxy group and/or amino group (particularly from a hydroxy group, primary amino group, or secondary amino group; particularly preferably hydroxy group(s)), with (ii) at least 3 molar equivalents of at least one polyether of formula (I)

$$T\text{-}K\text{-}A\text{-}K'\text{—}Y \tag{I}$$

wherein

A is a polyoxyalkylene chain made up of ethylene oxide units or of ethylene oxide units and propylene oxide units, having a maximum proportion of 50 wt % propylene oxide units based on the weight of A, K and K' are, mutually independently, a connectivity chosen from a covalent bond or from a molecule fragment having two free valences, T is a molecule fragment having at least one substituent chosen from
anionic residue,
—Si(OR)$_x$(R')$_{3-x}$ residue
wherein R and R' are, mutually independently, a (C$_1$ to C$_4$) alkyl group (particularly methyl or ethyl),
x is 1, 2, or 3, Y is a group reactive with respect to a hydroxy group or amino group, and (c) at least one nonionic film-forming and/or nonionic setting polymer encompassing at least one structural unit according to formula (M-I), at least one further structural unit according to formula (M-VII), and at least one further structural unit according to formula (M-VIII)

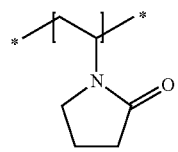

(M-I)

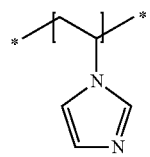

(M-VII)

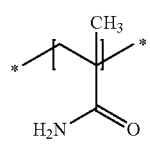

(M-VIII)

are very particularly preferably suitable in the context of this embodiment.

Those cosmetic agents containing, in a cosmetically acceptable carrier, (a) polyether-modified organic compounds obtained by reacting
(i) organic polyether polyol compounds having
at least three polyoxyalkylene chains made up of ethylene oxide units or of ethylene oxide units and propylene oxide units, having a maximum proportion of 50 wt % propylene oxide units based on the weight of the polyoxyalkylene chain,
at least three hydroxy groups
with
(ii) at least 3 molar equivalents of at least one compound of formula (III)

Y—K-T  (III)

wherein
Y is a group that is reactive with respect to OH, NH$_2$, NHR, NR$_2$,
K is a connectivity chosen from a covalent bond or from a molecule fragment having two free valences,
T is a molecule fragment having at least one substituent chosen from
anionic residue,
—Si(OR)$_x$(R')$_{3-x}$ residue
wherein R and R' are, mutually independently, a (C$_1$ to C$_4$) alkyl group (particularly methyl or ethyl),
x is 1, 2, or 3 and (a) at least one nonionic film-forming and/or nonionic setting polymer having at least one structural unit according to formula (M-I), at least one further structural unit according to formula (M-VII), and at least one further structural unit according to formula (M-VIII)

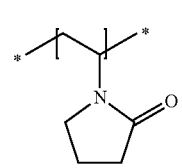

(M-I)

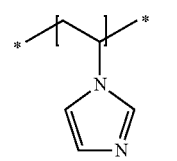

(M-VII)

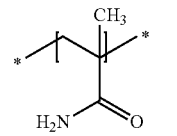

(M-VIII)

are furthermore considered in particular to be very particularly preferred in the context of this embodiment.

A particularly preferred polymer in this context is chosen from polymers having the INCI name VP/Methacrylamide/Vinyl Imidazole Copolymer, obtainable, for example, under the trade name Luviset Clear from the BASF SE Company.

It is furthermore preferred to use, in order to achieve the object, agents containing at least one nonionic film-forming and/or nonionic setting polymer having at least one structural unit of formula (M-I) and at least one structural unit of formula (M-III)

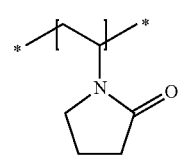

(M-I)

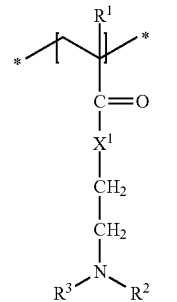

(M-III)

wherein
R¹ is a hydrogen atom or a methyl group,
X¹ is an oxygen atom or an NH group,
A¹ is an ethane-1,2-diyl, propane-1,3-diyl, or butane-1,4-diyl group,
R² and R³ are, mutually independently, a ($C_1$ to $C_4$) alkyl group.

Those agents containing, in a cosmetically acceptable carrier,
(a) polyether-modified organic compounds chosen from at least one compound of general formula (PE-1)

  (PE-1)

where Q, K', A, K, T, and n are defined as described previously,
and
(b) at least one nonionic film-forming and/or nonionic setting polymer having at least one structural unit according to formula (M-I) and at least one further structural unit according to formula (M-III)

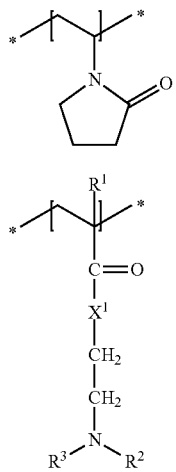

wherein
R¹ is a hydrogen atom or a methyl group,
X¹ is an oxygen atom or an NH group,
A¹ is an ethane-1,2-diyl, propane-1,3-diyl, or butane-1,4-diyl group,
R² and R³ are, mutually independently, a ($C_1$ to $C_4$) alkyl group
are furthermore considered in particular to be very particularly preferred in the context of this embodiment.

Those cosmetic agents containing, in a cosmetically acceptable carrier,
(a) polyether-modified organic compounds obtained by reacting
  (i) organic compounds containing at least three residues chosen from a hydroxy group and/or amino group (particularly from a hydroxy group, primary amino group, or secondary amino group; particularly preferably hydroxy group(s)), with
  (ii) at least 3 molar equivalents of at least one polyether of formula (I)

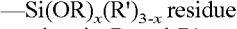  (I)

wherein
A is a polyoxyalkylene chain made up of ethylene oxide units or of ethylene oxide units and propylene oxide units, having a maximum proportion of 50 wt % propylene oxide units based on the weight of A,
K and K' are, mutually independently, a connectivity chosen from a covalent bond or from a molecule fragment having two free valences,
T is a molecule fragment having at least one substituent chosen from
  anionic residue,
  —Si(OR)$_x$(R')$_{3-x}$ residue
    wherein R and R' are, mutually independently, a ($C_1$ to $C_4$) alkyl group (particularly methyl or ethyl),
    x is 1, 2, or 3,
Y is a group reactive with respect to a hydroxy group or amino group,
and
(b) at least one nonionic film-forming and/or nonionic setting polymer having at least one structural unit according to formula (M-I) and at least one further structural unit according to formula (M-III)

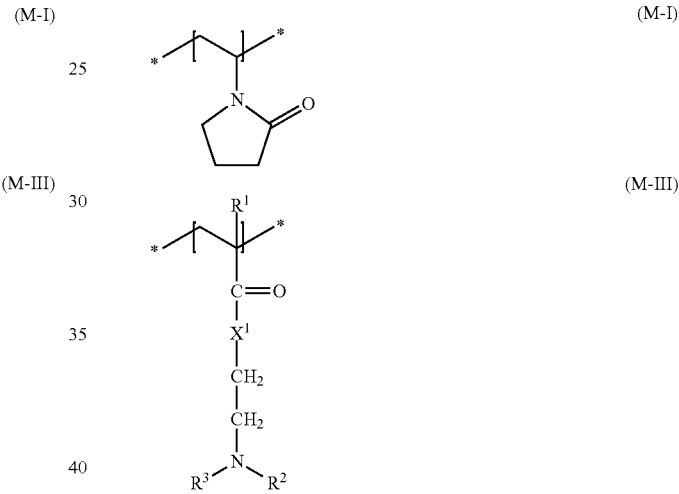

wherein
R¹ is a hydrogen atom or a methyl group,
X¹ is an oxygen atom or an NH group,
A¹ is an ethane-1,2-diyl, propane-1,3-diyl, or butane-1,4-diyl group,
R² and R³ are, mutually independently, a ($C_1$ to $C_4$) alkyl group
are very particularly preferably suitable in the context of this embodiment.

Those cosmetic agents containing, in a cosmetically acceptable carrier,
(b) polyether-modified organic compounds obtained by reacting
  (i) organic polyether polyol compounds having
    at least three polyoxyalkylene chains made up of ethylene oxide units or of ethylene oxide units and propylene oxide units, having a maximum proportion of 50 wt % propylene oxide units based on the weight of the polyoxyalkylene chain,
    at least three hydroxy groups
  with
  (ii) at least 3 molar equivalents of at least one compound of formula (III)

  (III)

wherein
Y is a group that is reactive with respect to OH, NH$_2$, NHR, NR$_2$,
K is a connectivity chosen from a covalent bond or from a molecule fragment having two free valences,
T is a molecule fragment having at least one substituent chosen from
anionic residue,
—Si(OR)$_x$(R')$_{3-x}$ residue
wherein R and R' are, mutually independently, a (C$_1$ to C$_4$) alkyl group (particularly methyl or ethyl),
x is 1, 2, or 3
and
(c) at least one nonionic film-forming and/or nonionic setting polymer having at least one structural unit according to formula (M-I) and at least one further structural unit according to formula (M-III)

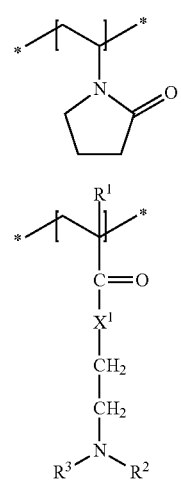

wherein
R$^1$ is a hydrogen atom or a methyl group,
X$^1$ is an oxygen atom or an NH group,
A$^1$ is an ethane-1,2-diyl, propane-1,3-diyl, or butane-1,4-diyl group,
R$^2$ and R$^3$ are, mutually independently, a (C$_1$ to C$_4$) alkyl group
are furthermore considered in particular to be very particularly preferred in the context of this embodiment.

It is particularly preferred if the above nonionic film-forming and/or nonionic setting polymer is chosen from at least one polymer that conforms to at least one or more of the following features:
R$^1$ is a methyl group,
X$^1$ is an NH group,
A$^1$ is ethane-1,2-diyl or propane-1,3-diyl,
R$^2$ and R$^3$ are, mutually independently, methyl or ethyl (particularly preferably methyl).

Particularly preferably, the nonionic film-forming and/or nonionic setting polymer of this embodiment is at least one polymer having at least one structural unit of formula (M-I) and at least one structural unit of formula (M-III-8)

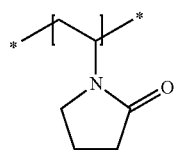

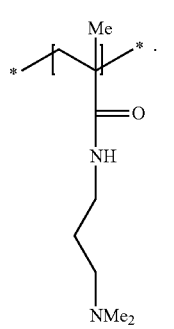

A very particularly preferred nonionic film-forming and/or nonionic setting polymer of this embodiment is a copolymer of N-vinylpyrrolidone and N,N-dimethylaminopropyl-methacrylamide that is sold, for example, with the INCI name VP/DMAPA Acrylates Copolymer, e.g., under the commercial designation Styleze® CC 10 by the ISP company.

In the context of all these aforementioned embodiments, the previously recited preferred embodiments of the polyether-modified organic compounds are preferably suitable (vide supra).

Similarly, all previously recited preferred quantitative indications with respect to components (a) and (b) of the agent are considered preferred for these embodiments as well, mutatis mutandis.

In a preferred embodiment, the agents contain as a film-forming and/or setting polymer at least one anionic film-forming and/or anionic setting polymer.

An "anionic" polymer is understood according to the present invention as a polymer that carries, in a protic solvent under standard conditions, structural units having anionic groups that must be compensated for by means of counterions to maintain electroneutrality, and comprises no structural units having permanently cationic or cationizable groups. "Anionic groups" includes carboxyl groups and sulfonic-acid groups.

The anionic film-forming and/or anionic setting polymers (b) are present in the agent preferably in a quantity from 0.1 wt % to 20.0 wt %, more preferably from 0.2 wt % to 15.0 wt %, particularly preferably from 0.5 wt % to 10.0 wt %, based on total weight of the agent according to the present invention.

It is preferred according to the present invention if the anionic film-forming and/or anionic setting polymer (b) contains at least one structural unit of formula (S1) that is chosen from at least one structural unit of formulas (S1-1) to (S1-5)

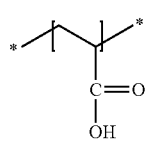

(S1-2)
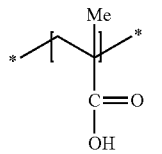
(S1-3)
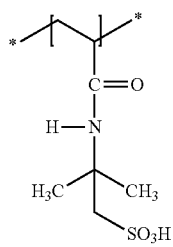
(S1-4)
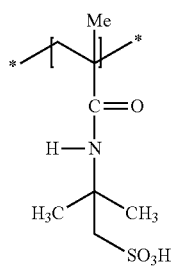
(S1-5)
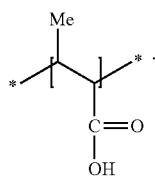
It is preferred according to the present invention if the anionic film-forming and/or anionic setting polymer (b) additionally contains, besides at least one structural unit of formulas (S1-1) to (S1-5), at least one structural unit of formula (S2) that is selected from at least one structural unit of formulas (S2-1) to (S2-8)
(S2-1)
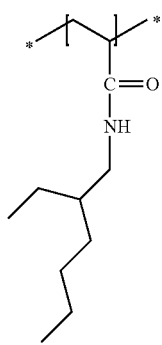
(S2-2)
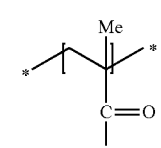
(S2-3)
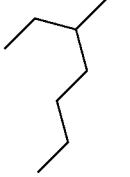
(S2-4)
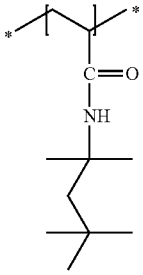
(S2-5)
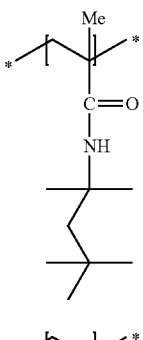
(S2-6)
(S2-7)
(S2-8)
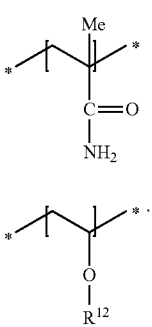

wherein $R^{12}$ is a ($C_2$ to $C_{12}$) acyl group (particularly acetyl or neodecanoyl).

In a preferred embodiment, those powdered compositions according to the present invention that contain, as a film-forming and/or setting polymer present in the form of particles, at least one polymer having at least one structural unit of formula (S1-5) and at least one structural unit of formula (S2-8)

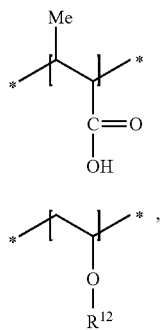
(S1-5)

(S2-8)

wherein $R^{12}$ is a ($C_2$ to $C_{12}$) acyl group (particularly acetyl or neodecanoyl),
are considered preferred according to the present invention.

Particularly preferred polymers of this kind are chosen from at least one polymer of the group that is constituted from
copolymers of vinyl acetate and crotonic acid,
copolymers of vinyl propionate and crotonic acid,
copolymers of vinyl neodecanoate, vinyl acetate, and crotonic acid.

Such copolymers are made available, for example, by the Clariant company under the commercial name Aristoflex A 60 (INCI name: VA/Crotonates Copolymer) in an isopropanol-water mixture (60 wt % active substance); by the BASF company under the commercial name Luviset CA 66 (vinyl acetate/crotonic acid copolymer 90:10, INCI name: VA/Crotonates Copolymer); and, by the National Starch company under the commercial name Resyn 28-2942 or Resyn 28-2930 (INCI name: VA/Crotonates/Vinyl Neodecanoate Copolymer).

Those agents containing, in a cosmetically acceptable carrier,
(a) polyether-modified organic compounds chosen from at least one compound of general formula (PE-1)

[Q-]-(-K'-A-K-T)$_n$ (PE-1)

where Q, K', A, K, T, and n are defined as described previously,
and
(b) at least one nonionic film-forming and/or nonionic setting polymer having at least one structural unit according to formula (S1-5) and at least one structural unit of formula (S2-8)

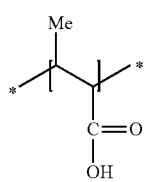
(S1-5)

-continued

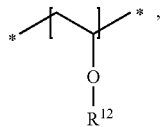
(S2-8)

wherein $R^{12}$ is a ($C_2$ to $C_{12}$) acyl group (particularly acetyl or neodecanoyl)
are furthermore considered in particular to be very particularly preferred in the context of this embodiment.

Those cosmetic agents containing, in a cosmetically acceptable carrier,
(a) polyether-modified organic compounds obtained by reacting
    (i) organic compounds containing at least three residues chosen from a hydroxy group and/or amino group (particularly from a hydroxy group, primary amino group, or secondary amino group; particularly preferably hydroxy group(s)), with
    (ii) at least 3 molar equivalents of at least one polyether of formula (I)

T-K-A-K'—Y (I)

wherein
A is a polyoxyalkylene chain made up of ethylene oxide units or of ethylene oxide units and propylene oxide units, having a maximum proportion of 50 wt % propylene oxide units based on the weight of A,
K and K' are, mutually independently, a connectivity chosen from a covalent bond or from a molecule fragment having two free valences,
T is a molecule fragment having at least one substituent chosen from
    anionic residue,
    —Si(OR)$_x$(R')$_{3-x}$ residue
        wherein R and R' are, mutually independently, a ($C_1$ to $C_4$) alkyl group (particularly methyl or ethyl),
        x is 1, 2, or 3,
Y is a group reactive with respect to a hydroxy group or amino group,
and
(a) at least one nonionic film-forming and/or nonionic setting polymer having at least one structural unit according to formula (S1-5) and at least one structural unit of formula (S2-8)

(S1-5)

(S2-8)

wherein $R^{12}$ is a ($C_2$ to $C_{12}$) acyl group (particularly acetyl or neodecanoyl)

are very particularly preferably suitable in the context of this embodiment.

Those cosmetic agents containing, in a cosmetically acceptable carrier, (a) polyether-modified organic compounds obtained by reacting
  (i) organic polyether polyol compounds having
    at least three polyoxyalkylene chains made up of ethylene oxide units or of ethylene oxide units and propylene oxide units, having a maximum proportion of 50 wt % propylene oxide units based on the weight of the polyoxyalkylene chain,
    at least three hydroxy groups
  with
  (ii) at least 3 molar equivalents of at least one compound of formula (III)

Y—K-T     (III)

wherein
Y is a group that is reactive with respect to OH, $NH_2$, NHR, $NR_2$,
K is a connectivity chosen from a covalent bond or from a molecule fragment having two free valences,
T is a molecule fragment having at least one substituent chosen from
  anionic residue,
  —$Si(OR)_x(R')_{3-x}$ residue
    wherein R and R' are, mutually independently, a ($C_1$ to $C_4$) alkyl group (particularly methyl or ethyl),
  x is 1, 2, or 3 and (b) at least one nonionic film-forming and/or nonionic setting polymer having at least one structural unit according to formula (S1-5) and at least one structural unit of formula (S2-8)

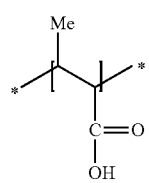   (S1-5)

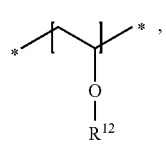   (S2-8)

wherein $R^{12}$ is a ($C_2$ to $C_{12}$) acyl group (particularly acetyl or neodecanoyl)
are furthermore considered in particular to be very particularly preferred in the context of this embodiment.

In a preferred embodiment, those powdered compositions according to the present invention that contain as an anionic film-forming and/or anionic setting polymer at least one polymer having at least one structural unit of formula (S1-1) and at least one structural unit of formula (S2-5)

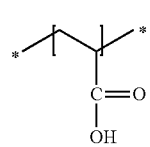   (S1-5)

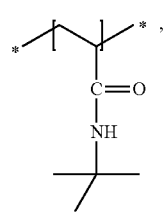   (S2-5)

are considered preferred according to the present invention.

It is in turn particularly preferred if the film-forming and/or setting polymer present in the form of particles additionally contains, besides the above structural units of formulas (S1-1) and (S2-5), at least one structural unit of formula (S3)

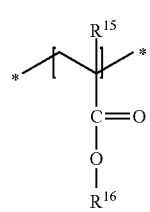   (S3)

wherein
$R^{15}$ is a hydrogen atom or a methyl group,
$R^{16}$ is a ($C_1$ to $C_4$) alkyl group (particularly a methyl group or an ethyl group).

Particularly preferred polymers of this kind are chosen from at least one polymer comprising copolymers of acrylic acid and ethyl acrylate and N-tert-butylacrylamide. Such polymers are made available, for example, by the BASF company under the commercial name Ultrahold® Strong (INCI name: Acrylates/t-Butylacrylamide Copolymer; white, pourable granules) or Ultrahold® 8 (INCI name: Acrylates/t-Butylacrylamide Copolymer; white, pourable granules).

Those agents containing, in a cosmetically acceptable carrier,
(a) polyether-modified organic compounds chosen from at least one compound of general formula (PE-1)

[Q—(—K'-A-K-T)$_n$     (PE-1)

where Q, K', A, K, T, and n are defined as described previously,
and
(b) at least one anionic film-forming and/or anionic setting polymer having at least one structural unit according to formula (S1-1) and at least one structural unit of formula (S2-5)

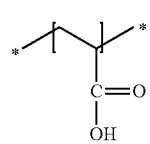   (S1-5)

-continued

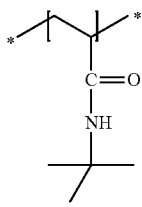
(S2-5)

are preferably suitable in the context of this embodiment.

Those cosmetic agents containing, in a cosmetically acceptable carrier,
(a) polyether-modified organic compounds obtained by reacting
(i) organic compounds containing at least three residues chosen from a hydroxy group and/or amino group (particularly from a hydroxy group, primary amino group, or secondary amino group; particularly preferably hydroxy group(s)), with
(ii) at least 3 molar equivalents of at least one polyether of formula (I)

T-K-A-K'—Y     (I)

wherein
A is a polyoxyalkylene chain made up of ethylene oxide units or of ethylene oxide units and propylene oxide units, having a maximum proportion of 50 wt % propylene oxide units based on the weight of A,
K and K' are, mutually independently, a connectivity chosen from a covalent bond or from a molecule fragment having two free valences,
T is a molecule fragment having at least one substituent chosen from
anionic residue,
—Si(OR)$_x$(R')$_{3-x}$ residue
wherein R and R' are, mutually independently, a ($C_1$ to $C_4$) alkyl group (particularly methyl or ethyl),
x is 1, 2, or 3,
Y is a group reactive with respect to a hydroxy group or amino group,
and
(c) at least one anionic film-forming and/or anionic setting polymer having at least one structural unit according to formula (S1-1) and at least one structural unit of formula (S2-5)

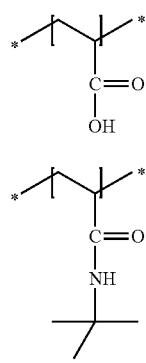

are preferably suitable in the context of this embodiment.

Those cosmetic agents containing, in a cosmetically acceptable carrier,
(a) polyether-modified organic compounds obtained by reacting
(i) organic polyether polyol compounds having
at least three polyoxyalkylene chains made up of ethylene oxide units or of ethylene oxide units and propylene oxide units, having a maximum proportion of 50 wt % propylene oxide units based on the weight of the polyoxyalkylene chain,
at least three hydroxy groups
with
(ii) at least 3 molar equivalents of at least one compound of formula (III)

Y—K-T     (III)

wherein
Y is a group that is reactive with respect to OH, $NH_2$, NHR, $NR_2$,
K is a connectivity chosen from a covalent bond or from a molecule fragment having two free valences,
T is a molecule fragment having at least one substituent chosen from
anionic residue,
—Si(OR)$_x$(R')$_{3-x}$ residue
wherein R and R' are, mutually independently, a ($C_1$ to $C_4$) alkyl group (particularly methyl or ethyl),
x is 1, 2, or 3
and
(d) at least one anionic film-forming and/or anionic setting polymer having at least one structural unit according to formula (S1-1) and at least one structural unit of formula (S2-5)

are preferably suitable in the context of this embodiment.

In one embodiment, those agents that contain, as an anionic film-forming and/or anionic setting polymer (b), at least one polymer having at least one structural unit of formula (S1-3) and at least one structural unit of formula (S2-6)

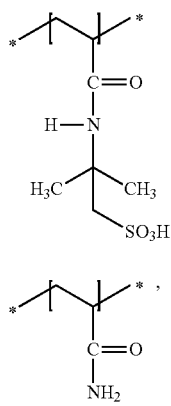

(S1-3)

(S2-6)

are preferred according to the present invention.

Preferred polymers (b) of this kind are chosen from at least one polymer of copolymers of 2-acrylamido-2-methylpropanesulfonic acid and acrylamide, copolymers of 2-acrylamido-2-methylpropanesulfonic acid and acrylic acid, copolymers of 2-acrylamido-2-methylpropanesulfonic acid, acrylamide, and methacrylic acid.

Polymers of this kind are marketed, for example, in an inverse isohexadecane emulsion by the Seppic company under the commercial name Sepigel® 305 (INCI name: Polyacrylamide, C13-14 Isoparaffin, Laureth-7) or Simulgel® 600 (INCI name: Acrylamide/Acryloyldimethyltaurate Copolymer, Isohexadecane, Polysorbate-80).

An agent particularly preferred according to the present invention contains, as polymer (b), a copolymer (b1).

These copolymers (b1) can be described by the general formula

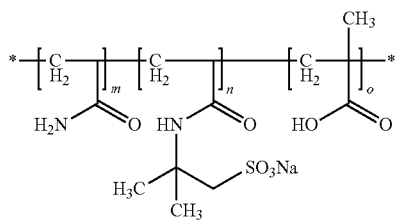

where m, n, and o each vary depending on the molar mass of the polymer and are not intended to signify that these are block copolymers. Structural units can instead be present in statistically distributed fashion in the molecule.

Particularly preferred agents according to the present invention are those wherein copolymer (b1) has a molar mass from 50 to 500 kDa, preferably 100 to 450 kDa, more preferably from 150 to 400 kDa, and in particular from 200 to 300 kDa.

Copolymers of acrylamide with methacrylic acid and acryloyldimethyl taurate are obtainable, for example, under the commercial name Acudyne® SCP (Rohm & Haas).

Those agents containing, in a cosmetically acceptable carrier, (a) polyether-modified organic compounds chosen from at least one compound of general formula (PE-1)

$$[Q+(-K'\text{-}A\text{-}K\text{-}T)_n \quad \text{(PE-1)}$$

where Q, K', A, K, T, and n are defined as described previously, and (b) at least one anionic film-forming and/or anionic setting polymer having at least one structural unit according to formula (S1-3) and at least one structural unit of formula (S2-6)

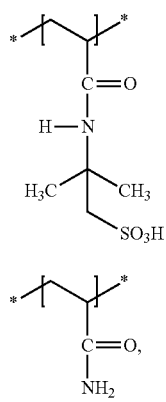

(S1-3)

(S2-6)

are preferably suitable in the context of this embodiment.

Those cosmetic agents containing, in a cosmetically acceptable carrier, (a) polyether-modified organic compounds obtained by reacting (i) organic compounds containing at least three residues chosen from a hydroxy group and/or amino group (particularly from a hydroxy group, primary amino group, or secondary amino group; particularly preferably hydroxy group(s)), with (ii) at least 3 molar equivalents of at least one polyether of formula (I)

$$\text{T-K-A-K'}\text{—Y} \quad \text{(I)}$$

wherein

A is a polyoxyalkylene chain made up of ethylene oxide units or of ethylene oxide units and propylene oxide units, having a maximum proportion of 50 wt % propylene oxide units based on the weight of A, K and K' are, mutually independently, a connectivity chosen from a covalent bond or from a molecule fragment having two free valences, T is a molecule fragment having at least one substituent chosen from anionic residue, —Si(OR)$_x$(R')$_{3-x}$ residue wherein R and R' are, mutually independently, a ($C_1$ to $C_4$) alkyl group (particularly methyl or ethyl), x is 1, 2, or 3, Y is a group reactive with respect to a hydroxy group or amino group, and (b) at least one anionic film-forming and/or anionic setting polymer having at least one structural unit according to formula (S1-3) and at least one structural unit of formula (S2-6)

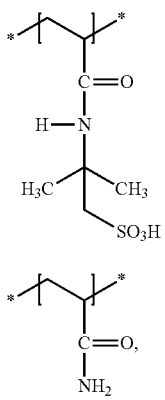
(S1-3)

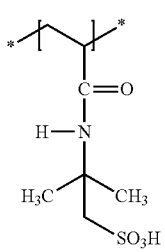
(S1-3)

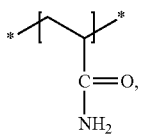
(S2-6)

are preferably suitable in the context of this embodiment.

Those cosmetic agents containing, in a cosmetically acceptable carrier,
(a) polyether-modified organic compounds obtained by reacting
(i) organic polyether polyol compounds having
at least three polyoxyalkylene chains made up of ethylene oxide units or of ethylene oxide units and propylene oxide units, having a maximum proportion of 50 wt % propylene oxide units based on the weight of the polyoxyalkylene chain,
at least three hydroxy groups
with
(ii) at least 3 molar equivalents of at least one compound of formula (III)

Y—K-T  (III)

wherein
Y is a group that is reactive with respect to OH, $NH_2$, NHR, $NR_2$,
K is a connectivity chosen from a covalent bond or from a molecule fragment having two free valences,
T is a molecule fragment having at least one substituent chosen from
anionic residue,
—$Si(OR)_x(R')_{3-x}$ residue
wherein R and R' are, mutually independently, a ($C_1$ to $C_4$) alkyl group (particularly methyl or ethyl),
x is 1, 2, or 3
and
(b) at least one anionic film-forming and/or anionic setting polymer having at least one structural unit according to formula (S1-3) and at least one structural unit of formula (S2-6)

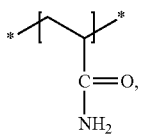
(S2-6)

are preferably suitable in the context of this embodiment.

In the context of these embodiments, the previously recited preferred embodiments of the polyether-modified organic compounds of formula (PE-1) are preferably suitable (vide supra).

Similarly, all previously recited preferred quantitative indications with regard to components (a) and (b) of the agent are considered preferred for these embodiments as well, mutatis mutandis.

In a preferred embodiment, agents according to the present invention contain as a film-forming and/or setting polymer at least one amphoteric film-forming and/or amphoteric setting polymer.

An "amphoteric polymer" is understood according to the present invention as a polymer that, in a protic solvent under standard conditions, carries structural units having anionic groups that must be compensated for by counterions to maintain electroneutrality, and additionally comprises structural units having groups cationizable by protonation but is free of permanently cationized groups. "Anionic" groups include carboxyl and sulfonic-acid groups. "Permanently cationized" nitrogen atoms are to be understood as those nitrogen atoms that carry a positive charge and thereby form a quaternary ammonium compound.

The amphoteric film-forming and/or amphoteric setting polymers (b) are present in the agents in a quantity from 0.1 wt % to 20.0 wt %, particularly preferably from 0.2 wt % to 15.0 wt %, very particularly preferably from 0.5 wt % to 10.0 wt %, based on total weight of the agent according to the present invention.

Preferably, the amphoteric film-forming and/or amphoteric setting polymer contains at least one structural unit of formula (S1) chosen from at least one structural unit of formulas (S1-1) to (S1-5)

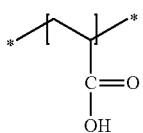
(S1-1)

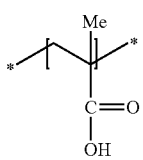
(S1-2)

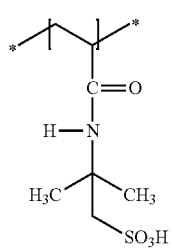
(S1-3)
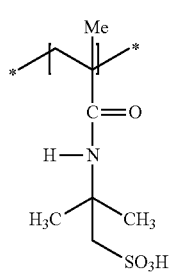
(S1-4)
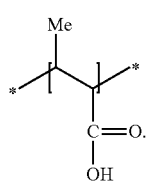
(S1-5)
It is particularly preferred if the amphoteric film-forming and/or amphoteric setting polymer additionally contains, besides at least one structural unit of formulae (S1-1) to (S1-5), at least one structural unit of formula (S2) chosen from at least one structural unit of formulae (S2-9) to (S2-15)
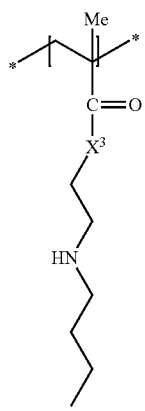
(S2-9)
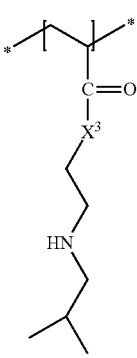
(S2-10)
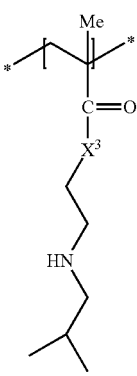
(S2-11)
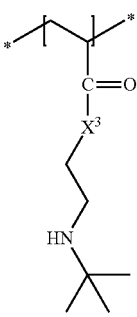
(S2-12)
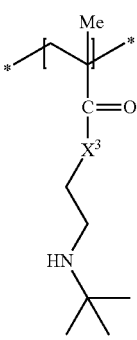
(S2-13)

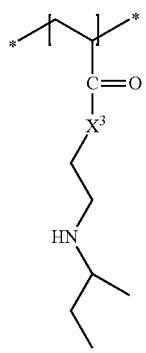 (S2-14)

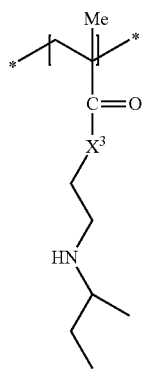 (S2-15)

wherein X³ is an oxygen atom or an NH group.

It is in turn particularly preferred according to the present invention if the amphoteric film-forming and/or amphoteric setting polymer additionally contains, besides at least one structural unit of formulae (S1-1) to (S1-5) and at least one structural unit of formulae (S2-9) to (S2-15), at least one structural unit of formulae (S2-1) to (S2-8)

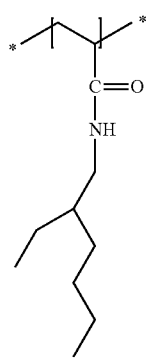 (S2-1)

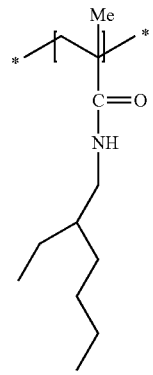 (S2-2)

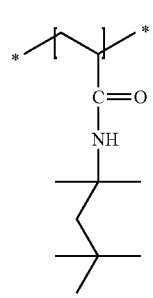 (S2-3)

(S2-4)

(S2-5)

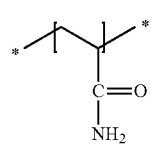 (S2-6)

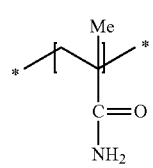 (S2-7)

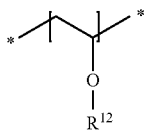
(S2-8)

wherein $R^{12}$ is a ($C_2$ to $C_{12}$) acyl group (in particular acetyl or neodecanoyl).

In a particularly preferred embodiment, the agent contains at least one amphoteric film-forming and/or amphoteric setting polymer having at least one structural unit of formula (S1-1), at least one structural unit of formula (S2-3), and at least one structural unit of formula (S2-16) (chosen in particular from the above formulae (S2-5) to (S2-12) with the provision that $X^3$ is an oxygen atom),

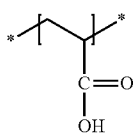
(S1-1)

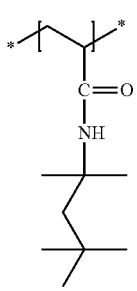
(S2-3)

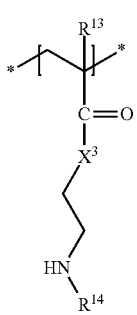
(S2-16)

wherein
$X^3$ is an oxygen atom or an NH group,
$R^{13}$ is a hydrogen atom or a methyl group, and
$R^{14}$ is an alkyl group having 4 carbon atoms (particularly n-butyl, sec-butyl, isobutyl, or tert-butyl).

It is in turn particularly preferred in this context if the amphoteric film-forming and/or anionic setting polymer additionally contains, besides the above structural units of formulas (S1-1), (S2-3), and (S2-16), at least one structural unit of formula (S3)

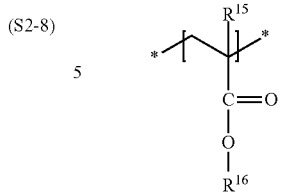
(S3)

wherein
$R^{15}$ is a hydrogen atom or a methyl group,
$R^{16}$ is a ($C_1$ to $C_4$) alkyl group (particularly a methyl group or an ethyl group).

Preferred polymers of this kind are chosen from copolymers of acrylic acid, ($C_1$ to $C_4$) alkyl acrylate, N—($C_4$ alkyl) aminoethyl methacrylate, and N—($C_8$ alkyl)acrylamide.

An example of a film-forming and/or setting polymer present in the form of particles and usable particularly preferably in this embodiment is the polymer obtainable under the trade name Amphomer® from the National Starch company, having the INCI name Octylacrylamide/Acrylates/Butylaminoethylmethacrylate Copolymer.

In the context of these embodiments, the previously recited preferred embodiments of the polyether of formula (I) are preferably suitable (vide supra).

Similarly, all the previously recited preferred quantitative indications with regard to components (a) and (b) of the agent according to the present invention are considered preferred for these embodiments as well, mutatis mutandis.

Those agents containing, in a cosmetically acceptable carrier, (a) polyether-modified organic compounds chosen from at least one compound of general formula (PE-1)

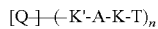
(PE-1)

where Q, K', A, K, T, and n are defined as described previously, and (b) at least one amphoteric film-forming and/or amphoteric setting polymer that contains at least one structural unit of formula (S1-1), at least one structural unit of formula (S2-3), and at least one structural unit of formula (S2-16) (selected in particular from the group that is constituted from the above formulas (S2-5) to (S2-12) with the provision that $X^3$ denotes an oxygen atom),

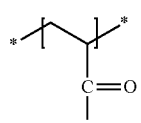
(S1-1)

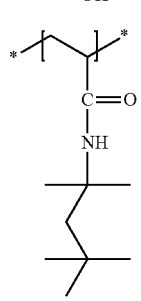
(S2-3)

-continued

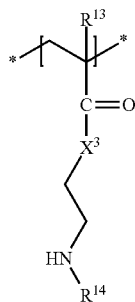
(S2-16)

wherein $X^3$ is an oxygen atom or an NH group, $R^{13}$ is a hydrogen atom or a methyl group, and $R^{14}$ is an alkyl group having 4 carbon atoms (particularly n-butyl, sec-butyl, isobutyl, or tert-butyl), are preferably suitable in the context of this embodiment.

Those cosmetic agents containing, in a cosmetically acceptable carrier, (a) polyether-modified organic compounds obtained by reacting (i) organic compounds containing at least three residues chosen from a hydroxy group and/or amino group (particularly from a hydroxy group, primary amino group, or secondary amino group; particularly preferably hydroxy group(s)), with (ii) at least 3 molar equivalents of at least one polyether of formula (I)

T-K-A-K'—Y         (I)

wherein

A is a polyoxyalkylene chain made up of ethylene oxide units or of ethylene oxide units and propylene oxide units, having a maximum proportion of 50 wt % propylene oxide units based on the weight of A, K and K' are, mutually independently, a connectivity chosen from a covalent bond or from a molecule fragment having two free valences, T is a molecule fragment having at least one substituent chosen from anionic residue, —Si(OR)$_x$(R')$_{3-x}$ residue wherein R and R' are, mutually independently, a (C$_1$ to C$_4$) alkyl group (particularly methyl or ethyl), x is 1, 2, or 3, Y is a group reactive with respect to a hydroxy group or amino group, and (b) at least one amphoteric film-forming and/or amphoteric setting polymer that contains at least one structural unit of formula (S1-1), at least one structural unit of formula (S2-3), and at least one structural unit of formula (S2-16) (selected in particular from the group that is constituted from the above formulas (S2-5) to (S2-12) with the provision that X$^3$ denotes an oxygen atom),

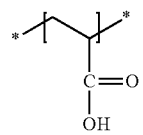
(S1-1)

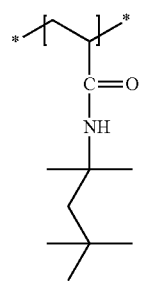
(S2-3)

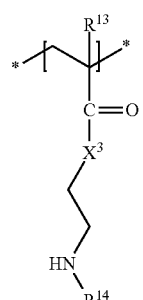
(S2-16)

wherein $X^3$ is an oxygen atom or an NH group, $R^{13}$ is a hydrogen atom or a methyl group, and $R^{14}$ is an alkyl group having 4 carbon atoms (particularly n-butyl, sec-butyl, isobutyl, or tert-butyl), are preferably suitable in the context of this embodiment.

Those cosmetic agents containing, in a cosmetically acceptable carrier, (a) polyether-modified organic compounds obtained by reacting (i) organic polyether polyol compounds having at least three polyoxyalkylene chains made up of ethylene oxide units or of ethylene oxide units and propylene oxide units, having a maximum proportion of 50 wt % propylene oxide units based on the weight of the polyoxyalkylene chain, at least three hydroxy groups with (ii) at least 3 molar equivalents of at least one compound of formula (III)

Y—K-T         (III)

wherein

Y is a group that is reactive with respect to OH, NH$_2$, NHR, NR$_2$,

K is a connectivity chosen from a covalent bond or from a molecule fragment having two free valences, T is a molecule fragment having at least one substituent chosen from anionic residue, —Si(OR)$_x$(R')$_{3-x}$ residue wherein R and R' are, mutually independently, a (C$_1$ to C$_4$) alkyl group (particularly methyl or ethyl), x is 1, 2, or 3 and (b) at least one amphoteric film-forming and/or amphoteric setting polymer that contains at least one structural unit of formula (S1-1), at least one structural unit of formula (S2-3), and at least one structural unit of formula (S2-16) (selected in particular from the group that is constituted from the above formulas (S2-5) to (S2-12) with the provision that $X^3$ denotes an oxygen atom),

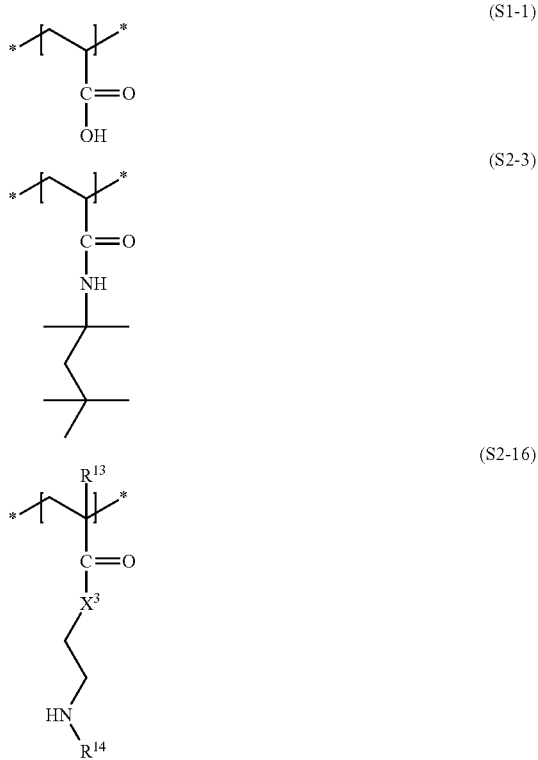

wherein $X^3$ is an oxygen atom or an NH group, $R^{13}$ is a hydrogen atom or a methyl group, and $R^{14}$ is an alkyl group having 4 carbon atoms (particularly n-butyl, sec-butyl, isobutyl, or tert-butyl), are preferably suitable in the context of this embodiment.

Agents according to the present invention contain the ingredients or active substances in a cosmetically acceptable carrier.

Preferred cosmetically acceptable carriers are aqueous, alcoholic, or aqueous alcoholic media preferably having at least 10 wt % water, based on total agent. Alcohols used can be, in particular, lower alcohols having 1 to 4 carbon atoms usually used for cosmetic purposes, for example, ethanol and isopropanol.

It is preferred according to the present invention to use at least one ($C_1$ to $C_4$) monoalkyl alcohol in the agents according to the present invention, in particular in a quantity from 1 to 50 wt %, in particular from 5 to 30 wt %. This is in turn particularly preferred for the presentation as a pump foam or aerosol foam.

Organic solvents or a mixture of solvents having a boiling point under 400° C. can be contained as additional co-solvents, in a quantity from 0.1 to 15 weight percent, preferably 1 to 10 weight percent, based on the entire agent. Unbranched or branched hydrocarbons such as pentane, hexane, isopentane, and cyclic hydrocarbons such as cyclopentane and cyclohexane, are particularly suitable as additional co-solvents. Further particularly preferred water-soluble solvents are glycerol, ethylene glycol, and propylene glycol, in a quantity of up to 30 wt % based on the entire agent.

The addition in particular of glycerol and/or propylene glycol and/or polyethylene glycol and/or polypropylene glycol increases the flexibility of the polymer film formed when the agent according to the present invention is used. If a flexible hold is desired, the agents according to the present invention therefore by preference contain 0.01 to 30 wt % glycerol and/or propylene glycol and/or polyethylene glycol and/or polypropylene glycol, based on the entire agent.

The agents preferably have a pH from 2 to 11. Particularly preferably, the pH range is between 2 and 8. The indications as to pH refer here, for purposes of this document, to the pH at 25° C. unless otherwise noted.

The agents according to the present invention can furthermore contain the adjuvants and additives that are usually added to conventional styling agents.

The agents according to the present invention additionally contain by preference at least one surfactant; nonionic, anionic, cationic, and ampholytic surfactants are suitable in principle. The group of the ampholytic or also amphoteric surfactants encompasses zwitterionic surfactants and ampholytes. The surfactants can, according to the present invention, already have an emulsifying effect.

The additional surfactants are present in the agent preferably in a quantity from 0.01 wt % to 5 wt %, particularly preferably from 0.05 wt % to 0.5 wt %, based on total weight of the agent.

It has proven to be particularly preferred if agents according to the present invention additionally contain at least one nonionic surfactant.

Nonionic surfactants contain as a hydrophilic group, for example, a polyol group, a polyalkylene glycol ether group, or a combination of a polyol and polyglycol ether group. The alkylene oxide addition products with saturated linear fatty alcohols and fatty acids, having in each case 2 to 100 mol ethylene oxide per mol of fatty alcohol resp. fatty acid, have proven to be very particularly preferred nonionic surfactants. Preparations having outstanding properties are likewise obtained when they contain, as nonionic surfactants, $C_{12}$ to $C_{30}$ fatty acid mono- and diesters of addition products of 1 to 30 mol ethylene oxide with glycerol and/or addition products of 5 to 60 mol ethylene oxide with castor oil and hardened castor oil.

In the case of the surfactants that represent addition products of ethylene oxide and/or propylene oxide with fatty alcohols, or derivatives of said addition products, both products having a "normal" homolog distribution and those having a restricted homolog distribution can be used. A "normal" homolog distribution is understood here as mixtures of homologs that are obtained upon reaction of fatty alcohol and alkylene oxide using alkali metals, alkali metal hydroxides, or alkali metal alcoholates as catalysts. Restricted homolog distributions, on the other hand, are obtained when, for example, hydrotalcites, alkaline-earth metal salts of ethercarboxylic acids, or alkaline-earth metal oxides, hydroxides, or alcoholates are used as catalysts. The use of products having a restricted homolog distribution can be preferred.

Very particularly preferably, the agents according to the present invention contain as a surfactant at least one addition product of 15 to 100 mol ethylene oxide, in particular 15 to 50 mol ethylene oxide, with a linear or branched (in particular linear) fatty alcohol having 8 to 22 carbon atoms. This refers very particularly preferably to ceteareth-15, ceteareth-25, or ceteareth-50, which are marketed as Eumulgin® CS 15 (COGNIS), Cremophor A25 (BASF SE), resp. Eumulgin® CS 50 (COGNIS).

All anionic surface-active substances suitable for use on the human body are, in principle, appropriate as anionic surfactants. These are characterized by an anionic group imparting water solubility, for example a carboxylate, sulfate, sulfonate, or phosphate group, and a lipophilic alkyl group having approximately 8 to 30 carbon atoms. Glycol ether or polyglycol ether groups, ester, ether, and amide groups, and hydroxy groups can additionally be contained in the molecule.

Preferred anionic surfactants are alkyl sulfates, alkyl polyglycol ether sulfates, and ethercarboxylic acids having 10 to 18 carbon atoms in the alkyl group and up to 12 glycol ether groups in the molecule, sulfosuccinic acid mono- and dialkyl esters having 8 to 18 carbon atoms in the alkyl group, and sulfosuccinic acid monoalkylpolyoxyethyl esters having 8 to 18 carbon atoms in the alkyl group and 1 to 6 oxyethyl groups, monoglycerol disulfates, alkyl and alkenyl ether phosphates, as well as protein fatty acid condensates.

Cationic surfactants of the quaternary ammonium compound, esterquat, and amidoamine types are furthermore usable according to the present invention. Preferred quaternary ammonium compounds are ammonium halides, in particular chlorides and bromides, such as alkyltrimethylammonium chlorides, dialkyldimethylammonium chlorides, and trialkylmethylammonium chlorides. The long alkyl chains of these surfactants preferably comprise 10 to 18 carbon atoms, for example as in cetyltrimethylammonium chloride, stearyltrimethylammonium chloride, distearyldimethylammonium chloride, lauryldimethylammonium chloride, lauryldimethylbenzylammonium chloride, and tricetylmethylammonium chloride. Further preferred cationic surfactants are the imidazolium compounds known by the INCI names Quaternium-27 and Quaternium-83.

"Zwitterionic surfactants" refers to those surface-active compounds that carry in the molecule at least one quaternary ammonium group and at least one —COO$^{(-)}$ or SO$_3^{(-)}$ group. Particularly suitable zwitterionic surfactants are the so-called betaines, such as the N-alkyl-N,N-dimethylammonium glycinates, for example cocalkyldimethylammonium glycinate, N-acylaminopropyl-N,N-dimethylammonium glycinates, for example cocacylaminopropyldimethylammonium glycinate, and 2-alkyl-3-carb oxymethyl-3-hydroxyethylimidazolines, having in each case 8 to 18 carbon atoms in the alkyl or acyl group, as well as cocacylaminoethylhydroxyethylcarboxymethyl glycinate. A preferred zwitterionic surfactant is the fatty acid amide derivative known by the INCI name Cocamidopropyl Betaine.

"Ampholytes" are understood to be those surface-active compounds that contain in the molecule, in addition to a C$_8$ to C$_{24}$ alkyl or acyl group, at least one free amino group and at least one —COOH or —SO$_3$H group, and are capable of forming internal salts. Examples of suitable ampholytes are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids, and alkylaminoacetic acids, having in each case approximately 8 to 24 carbon atoms in the alkyl group. Particularly preferred ampholytes are N-cocalkylaminopropionate, cocacylaminoethylaminopropionate, and C$_{12}$ to C$_{18}$ acyl sarcosine.

Additional care-providing substances may be recited in particular as further suitable adjuvants and additives.

A silicone oil and/or a silicone gum can be used, for example, as a care-providing substance.

Silicone oils or silicone gums that are suitable according to the present invention are, in particular, dialkyl- and alkylarylsiloxanes, for example dimethylpolysiloxane and methylphenylsiloxane, as well as alkoxylated, quaternized, or also anionic derivatives thereof. Cyclic and linear polydialkylsiloxanes, alkoxylated and/or aminated derivatives thereof, dihydroxylpolydimethylsiloxanes, and polyphenylalkylsiloxanes are preferred. The agents contain the silicones preferably in quantities from 0.01 wt % to 15 wt %, particularly preferably from 0.05 to 2 wt %, based on the entire agent.

The agent can contain as a care-providing substance of a different compound class, for example, at least one protein hydrolysate and/or a derivative thereof. Protein hydrolysates are product mixtures obtained by the acid-, base-, or enzyme-catalyzed breakdown of proteins. The term "protein hydrolysates" is also understood according to the present invention to mean total hydrolysates as well as individual amino acids and derivatives thereof, as well as mixtures of different amino acids. Polymers constructed from amino acids and amino-acid derivatives are also understood according to the present invention under the term "protein hydrolysates". The molecular weight of the protein hydrolysates usable according to the present invention is between 75 (the molecular weight of glycine) and 200,000; the molecular weight is preferably 75 to 50,000 dalton, and very particularly preferably 75 to 20,000 dalton. The protein hydrolysates are contained in the agents according to the present invention, for example, in concentrations from 0.01 wt % to 20 wt %, by preference from 0.05 wt % to 15 wt %, and very particularly preferably in quantities from 0.05 wt % to 5 wt %, based in each case on the entire application preparation.

The agent according to the present invention can further contain at least one vitamin, one provitamin, one vitamin precursor, and/or one derivative thereof as a care-providing substance. Those vitamins, provitamins, and vitamin precursors that are usually assigned to groups A, B, C, E, F, and H are preferred according to the present invention. The agents according to the present invention preferably contain vitamins, provitamins, and vitamin precursors from groups A, B, C, E, and H. Panthenol, pantolactone, pyridoxine and derivatives thereof, as well as nicotinic acid amide and biotin, are particularly preferred. Very particularly preferably, D-panthenol is used as a care-providing substance, optionally in combination with at least one of the silicone derivatives recited above.

Like the addition of glycerol and/or propylene glycol, the addition of panthenol also enhances the flexibility of the polymer film formed upon utilization of the agent according to the present invention. If a particularly flexible hold is desired, the agents according to the present invention can thus contain panthenol instead of or in addition to glycerol and/or propylene glycol. In a preferred embodiment the agents according to the present invention contain panthenol, by preference in a quantity from 0.05 to 10 wt %, particularly preferably 0.1 to 5 wt %, based in each case on the entire agent.

Agents according to the present invention can further contain at least one plant extract as a care-providing substance.

These extracts are usually produced by extraction of the entire plant. In individual cases, however, it may also be preferred to produce the extracts exclusively from blossoms and/or leaves of the plant. According to the present invention the extracts from green tea, oak bark, nettle, hamamelis, hops, henna, chamomile, burdock root, horsetail, hawthorn, linden blossoms, almond, aloe vera, pine needles, horse chestnut, sandalwood, juniper, coconut, mango, apricot, lemon, wheat, kiwi fruit, melon, orange, grapefruit, salvia, rosemary, birch, mallow, lady's-smock, wild thyme, yarrow, thyme, lemon balm, restharrow, coltsfoot, hibiscus, meristem, ginseng, and ginger root are especially preferred.

Ectoin or ectoin derivatives, allantoin, taurine, and/or bisabolol are also suitable as a care-providing substance.

Agents according to the present invention contain these care-providing substances preferably in quantities from 0.001 to 2 wt %, particularly from 0.01 to 0.5 wt %, based on total application preparation.

Oily substances are furthermore suitable as a care-providing substance. The quantity of natural and synthetic cosmetic oily substances to be used in the agents according to the present invention is usually equal to 0.1 to 30 wt % based on the entire application preparation, preferably 0.1 to 20 wt % and in particular 0.1 to 15 wt %.

Although each of the aforesaid care-providing substances already yields a satisfactory result of itself, all embodiments in which the agent contains multiple care-providing substances, including from different groups, are also encompassed within the scope of the present invention.

The addition of a UV filter allows both the agents themselves, and the treated fibers, to be protected from damaging influences of UV radiation. At least one UV filter is therefore by preference added to the agent. The suitable UV filters are not subject to any general restrictions in terms of their structure and their physical properties. Instead, all UV filters usable in the cosmetics sector, whose absorption maximum lies in the UVA (315 to 400 nm) UVB (280 to 315 nm), or UVC (<280 nm) regions, are suitable. UV filters having an absorption maximum in the UVB region, in particular in the region from approximately 280 to approximately 300 nm, are particularly preferred. The UV filters preferred according to the present invention can be selected, for example, from substituted benzophenones, p-aminobenzoic acid esters, diphenylacrylic acid esters, cinnamic acid esters, salicylic acid esters, benzimidazoles, and o-aminobenzoic acid esters.

UV filters are contained usually in quantities from 0.01 to 5 wt %, based on total application preparation. Quantities from 0.1 to 2.5 wt % are preferred.

Agents according to the present invention according to this embodiment contain the substantive dyes preferably in a quantity from 0.001 to 20 wt %, based on total agent.

Preferably, agents according to the present invention are free of oxidation dye precursor products. Oxidation dye precursor products are divided into developer components and coupler components. The developer components form the actual dyes with one another under the influence of oxidizing agents or atmospheric oxygen, or by coupling with one or more coupler components.

In addition to the components recited, the agents can also contain all active substances, additives, and adjuvants known for such preparations.

Agents according to the present invention can be formulated in any form usual for cosmetic agents, for example, in the form of solutions that can be applied onto the hair as a hair lotion or as a pump or aerosol spray, in the form of creams, emulsions, waxes, gels, or also surfactant-containing foaming solutions or other preparations suitable for application to the hair.

Hair creams and hair gels generally contain structuring agents and/or thickening polymers which serve to impart the desired consistency to the products. Structuring agents and/or thickening polymers are typically used in a quantity from 0.1 to 10 wt %, based on total product. Quantities from 0.5 to 5 wt %, particularly 0.5 to 3 wt %, are preferred.

The agents according to the present invention are preferably presented as a pump spray, aerosol spray, pump foam, or aerosol foam.

For this purpose, the agents according to the present invention are packaged in a delivery apparatus that represents either a pressurized gas container additionally filled with a propellant ("aerosol container"), or a non-aerosol container.

The pressurized gas container with which a product is distributed through a valve as a result of the internal gas pressure of the container is referred to as an "aerosol container." A "non-aerosol container" is defined, conversely to the "aerosol" definition, as a vessel under standard pressure with which a product is distributed by mechanical action by way of a pump system.

Agents according to the present invention are present particularly preferably as an aerosol hair foam or aerosol hair spray. The agent therefore preferably additionally contains at least one propellant. Propellants suitable according to the present invention include $N_2O$, dimethyl ether, $CO_2$, air, alkanes having 3 to 5 carbon atoms such as propane, n-butane, isobutane, n-pentane, and isopentane, and mixtures thereof. Dimethyl ether, propane, n-butane, isobutane, and mixtures thereof are preferred.

According to a preferred embodiment, the aforesaid alkanes, mixtures of the aforesaid alkanes, or mixtures of the aforesaid alkanes with dimethyl ether are used as the only propellant. The invention also expressly includes, however, the concurrent use of propellants of the chlorofluorocarbon type, particularly fluorocarbons.

For a given spray apparatus, the sizes of the aerosol droplets or foam bubbles and the respective size distribution can be adjusted by the quantitative ratio between the propellant and other constituents of the preparations. The quantity of propellant used varies as a function of the specific composition of the agent, the packaging used, and the desired type of product (e.g., hair spray or hair foam). When conventional spray apparatuses are used, aerosol foam products preferably contain propellant in quantities from 1 to 35 wt %, based on total product. Quantities from 2 to 30 wt %, particularly from 3 to 15 wt %, are particularly preferred. Aerosol sprays generally contain larger quantities of propellant. In this case, the propellant is preferably used in a quantity from 30 to 98 wt %, based on total product. Quantities from 40 to 95 wt %, in particular from 50 to 95 wt %, are particularly preferred.

Aerosol products can be manufactured in typical fashion. As a rule, all ingredients of the particular agent, with the exception of the propellant, are introduced into a suitable pressure-tight container. The container is then sealed with a valve. Lastly, the desired quantity of propellant is introduced using conventional techniques.

In order to foam gel-type agents in a two-chamber aerosol container, isopentane is preferably suitable as a propellant that is incorporated into the agents and is packaged in the first chamber of the two-chamber aerosol container. Packaged in the second chamber of the two-chamber aerosol container is at least one further propellant different from isopentane and that builds up in the two-chamber aerosol container a pressure higher than the isopentane. The propellants of the second chamber are preferably chosen from $N_2O$, dimethyl ether, $CO_2$, air, alkanes having 3 or 4 carbon atoms (such as propane, n-butane, isobutane), and mixtures thereof.

Agents according to the present invention and products that contain said agents, particularly aerosol hair foams or aerosol hairsprays and gels, impart to treated hair a very strong, durable hairstyle hold even though the hair remains flexible.

A second subject of the invention is the use of agents according to the present invention for temporary deformation of hair and/or for hair care.

A third subject of the invention is the use of polyether-modified organic compounds according to a first subject of the invention against greasy skin and/or against greasy hair (preferably against greasy hair).

Skin grease stain repellency on the skin and/or on the hair (preferably on the hair) is increased by the aforesaid polyethers. It is preferred in this context to use cosmetic agents that contain, besides at least one of the aforesaid polyethers, at least one surfactant.

It is likewise preferred according to the present invention to use, instead of the polyether of formula (I), at least one compound that has been manufactured according to the manufacturing method described in the first subject of the invention. A mixture of reaction products from the above manufacturing method can also be used in this context.

The polyethers characterized as preferred according to the first subject of the invention are also preferably suitable here. The same applies to the surfactants mentioned in the first subject of the invention. The presence of at least one anionic surfactant is preferred in this context.

A fourth subject of the invention is the use of the agent according to the first subject of the invention to improve hairstyle hold.

Agents according to the present invention characterized as preferred according to the first subject of the invention are also preferably suitable here.

The Examples that follow are intended to explain the subject matter of the present invention without in any way limiting it.

EXAMPLES

The molecular weights indicated in the Examples section are number-average molecular weights of the initial compounds (polyether polyols) that were used to manufacture the prepolymers. The number-average molecular weight of the polyols can be determined computationally by terminal group determination, based on a knowledge of the functionality of the compounds or the functionality of the mixture components, and the OH number of the compound or of the mixture (ascertained according to DIN 53240). For the case in which, instead of the polyols, other compounds are used as initial compounds, their number-average molecular weight is what applies. For example, the number-average molecular weight of amines can be ascertained via a terminal group determination by potentiometric titration according to DIN 16945.

Manufacture of Suitable Star-Shaped Prepolymers

Example 1

Three-Armed Triethyoxysilyl-Terminated Polyethers (PP1)

The polyether polyol used is a three-armed poly(ethylene oxide co-propylene oxide) having an EO/PO ratio of 75/25 and a number-average molecular weight of approx. 5000 g/mol, obtained from the DOW Chemical company (Voranol® CP 1421). Before reacting, the polyol was heated under vacuum to 80° C. for 1 hour while stirring.

(3-Isocyanatopropyl)triethoxysilane (317 mg, 1.0 eq.) was slowly added to the dried polyether polyol (2.04 g, 0.41 mmol). The reaction mixture was further stirred under inert gas at 100° C. for 2 days, until the vibrational band of the NCO group in an IR measurement had disappeared. What is obtained is a product in which a triethoxysilyl group is present at each of the free ends of the polymer arms of the star-shaped prepolymer. The product is a colorless, viscous liquid.

Example 2

Six-Armed Triethoxysilyl-Terminated Polyether (PP2)

The polyether polyol used is a six-armed poly(ethylene oxide co-propylene oxide) having an EO/PO ratio of 80/20 and a molecular weight of 12,000 g/mol, manufactured by anionic ring-opening polymerization of ethylene oxide and propylene oxide using sorbitol as initiator. Before reacting, the polyol was heated under vacuum to 80° C. for 1 h while stirring.

A solution of polyether polyol (3 g, 0.25 mmol), triethylenediamine (9 mg, 0.081 mmol), and dibutyltin dilaurate (9 mg, 0.014 mmol) in 25 ml anhydrous toluene was prepared, and a solution of (3-isocyanatopropyl)triethoxysilane (0.6 ml, 2.30 mmol) in 10 ml anhydrous toluene was added to it dropwise. The solution was further stirred overnight at 50° C. After removal of the toluene under vacuum, the raw product was repeatedly washed with anhydrous ether. Vacuum drying yielded the product, which comprises a triethoxysilyl group at each of the free ends of the polymer arms of the star-shaped prepolymer, as a colorless, viscous liquid. IR (film, cm$^{-1}$): 3349 (m, —CO—NH—), 2868 (s, —CH$_2$—, —CH$_3$), 1719 (s, —C=O), 1456 (m, —CH$_2$—, —CH$_3$), 1107 (s, —C—O—C—), 954 (m, —Si—O—). $^1$H-NMR (benzene-d$_6$, ppm): 1.13 (d, —CH$_3$ of polymer arms), 1.21 (t, —CH$_3$ of silane terminal groups), 3.47 (s, —CH$_2$ of polymer arms), 3.74 (q, —CH$_2$ of silane terminal groups).

Example 3

Six-Armed Triethoxysilyl-/Hydroxy-Terminated Polyether (PP3)

Analogously to Example 2, a solution of polyether polyol (10 g, 0.83 mmol), triethylenediamine (30 mg, 0.27 mmol), and dibutyltin dilaurate (30 mg, 0.048 mmol) in 50 ml anhydrous toluene was prepared, and a solution of (3-isocyanatopropyl)triethoxysilane (0.65 ml, 2.49 mmol) in 15 ml anhydrous toluene was added to it dropwise. The solution was further stirred overnight at 50° C. After removal of the toluene under vacuum, the raw product was analyzed by IR. The results showed that the typical vibrations of the NCO group at approx. 2270 cm$^{-1}$ had completely disappeared, and reduced OH vibrations were consequently visible at approx. 3351 cm$^{-1}$, indicating that the isocyanatosilane molecules are successfully linked via a urethane bond to the ends of the polyol. The raw product was then repeatedly washed with anhydrous ether. Vacuum drying yielded the product, which comprises triethoxysilyl and hydroxy groups at a statistical ratio of 3:3 at each of the free ends of the polymer arms of the star-shaped prepolymer, as a colorless, viscous liquid. IR (film, cm$^{-1}$): 3511 (m, —OH), 3351 (m, —CO—NH—), 2868 (s, —CH$_2$—, —CH$_3$), 1720 (s, —C=O), 1456 (m, —CH$_2$—, —CH$_3$), 1112 (s, —C—O—C—), 953 (m, —Si—O—). $^1$H-NMR (benzene-d$_6$, ppm): 1.08 to 1.17 (m, —CH$_3$ of polymer arms and —CH$_3$ of silane terminal groups), 3.47 (s, —CH$_2$ of polymer arms), 3.74 (q, —CH$_2$ of silane terminal groups).

Example 4

Six-Armed Triethoxysilyl-/Hydroxy-Terminated Polyether (PP4)

Analogously to Example 2, a solution of polyether polyol (10 g, 0.83 mmol), triethylenediamine (30 mg, 0.27 mmol), and dibutyltin dilaurate (30 mg, 0.048 mmol) in 50 ml anhydrous toluene was prepared. A solution of (3-isocyanatopropyl)triethoxysilane (0.22 ml, 0.84 mmol) in 15 ml anhydrous toluene was added to it dropwise. The solution was further stirred overnight at 50° C. After removal of the toluene under vacuum, the raw product was repeatedly washed with anhydrous ether. Vacuum drying yielded the product, which comprises triethoxysilyl and hydroxy groups at a statistical ratio of 1:5 at each of the free ends of the polymer arms of the star-shaped prepolymer, as a colorless, viscous liquid. IR (film, cm$^{-1}$): 3494 (m, —OH), 3346 (m, —CO—NH—), 2868 (s, —CH$_2$—, —CH$_3$), 1722 (m, —C=O), 1456 (m, —CH$_2$—, —CH$_3$), 1112 (s, —C—O—C—), 952 (m, —Si—O—). $^1$H-NMR (benzene-d$_6$, ppm): 1.08 to 1.18 (m, —CH$_3$ of polymer arms and —CH$_3$ of silane terminal groups), 3.49 (s, —CH$_3$ of polymer arms), 3.75 (q, —CH$_2$ of silane terminal groups).

Example 5

Six-Armed Triethoxysilyl-Terminated Polyether (PP5)

The polyether polyol used is a six-armed statistical poly(ethylene oxide co-propylene oxide) having an EO/PO ratio of approx. 80/20 and a number-average molecular weight of approx. 3000 g/mol, manufactured by anionic ring-opening polymerization of ethylene oxide and propylene oxide using sorbitol as initiator. Before reacting, the polyether polyol was heated under vacuum to 80° C. for 1 h while stirring.

Dibutyltin laurate (2 mg, 0.01%) and (3-isocyanatopropyl) triethoxysilane (9.5 g, 1.0 eq.) was slowly added to the dried polyether polyol (20 g, 6.67 mmol). The reaction mixture was further stirred under inert gas at 100° C. for 2 days, until the NCO band in an IR measurement had disappeared. The product obtained, which comprises a triethoxysilyl group at each of the free ends of the polymer arms of the star-shaped prepolymer, was a colorless, viscous liquid.

Example 6

Mixture of Three-Armed Triethoxysilyl-Terminated Polyether and Eight-Armed Triethoxysilyl-Terminated Polyether (PP6)

The polyether polyol mixture used is made up of a three-armed statistical poly(ethylene oxide co-propylene oxide) (glycerol-initiated) and an eight-armed polyether polyol (raw sugar-initiated). The polymer arms are in each case statistical poly(ethylene oxide co-propylene oxides) having an EO/PO ratio of 75/25. The OH functionality is on average 6.9 (ascertained by terminal group determination), yielding an average number-average molecular weight of approx. 12,000 g/mol. The result is a ratio of 78 wt % eight-armed polyether polyol to 22 wt % three-armed polyether polyol. The polyether polyol mixture was obtained from the DOW Chemical company (Voranol® 4053). Before reacting, the polyether polyol was heated under vacuum to 80° C. for 1 h while stirring.

Dibutyltin laurate (20.9 mg, 0.01%) and (3-isocyanatopropyl)triethoxysilane (30.3 g, 1.0 eq.) was slowly added to the dried polyether polyol (209 g, 16.9 mmol). The reaction mixture was further stirred under inert gas at 100° C. for 2 days, until the vibrational band of the NCO group in an IR measurement had disappeared. The product obtained, in which a triethoxysilyl group is present at each of the free ends of the polymer arms of the two star-shaped prepolymers, was a colorless, viscous liquid.

Measuring the Static Water Contact Angle and Contact Angle Hysteresis—

Measurements were carried out with a contact angle measurement instrument of DataPhysics GmbH (model OCA-20; electronic tilting apparatus: TBU90E; electronic syringe module ES; software: SCA including software update for SCA modules (version 3.11.6, build 155)).

Prior to measurement, the instrument was calibrated using its automatic calibration system. A drop of distilled water (15 µl) was applied, by means of the syringe module, onto the surface of the specimen carrier to be measured. The tilt angle is 0°, i.e. the area to be measured is horizontal. An image of the drop is acquired using a video camera. On the frame image, the software places a tangent to the drop cross section at the point at which the drop touches the surface. The angle thereby obtained between the tangent and the surface to be measured is referred to as the "static" contact angle (sessile drop method).

The sample, together with the sample plate and camera, are then tilted at the slowest speed allowed by the instrument (calculated from instrument data as 0.62°/s) to an angle of 90°. During this process, a video of the drop is recorded by the camera using the software, the tilt angle at the recording time being concurrently saved. Measurement is terminated as soon as the drop begins to run off the surface. Using the software, the advancing contact angle (angle in the drop flow direction) and retreating contact angle (on the other side of the drop), at the moment when the drop begins to run off the surface, are determined in the video with the measurement software's ellipse method. The difference between the two angles is the contact angle hysteresis (tilting plate method).

Preparation of Hair Treatment Agents—

The following hair treatment agents were manufactured by mixing the ingredients:

TABLE 1

Hair gel

| Raw material | Wt % |
| --- | --- |
| Benzophenone-4 | 0.05 |
| Synthalen K | 1.0 |
| Neolone PE | 0.6 |
| PP1 | 1.0 |
| PVP/VA Copolymer 60/40 W | 5.0 |
| Luviskol K 85 CQ solution | 4.0 |
| Dow Corning 193 Fluid | 0.2 |
| Neutrol TE | 1.3 |
| Antara 430 | 0.1 |
| D-Panthenol | 0.1 |
| PEG-40 Hydrogenated Castor Oil | 0.5 |
| Perfume | 0.2 |
| Water | to 100 |

TABLE 2

Hair gel

| Raw material | Wt % |
| --- | --- |
| Benzophenone-4 | 0.05 |
| Synthalen K | 0.5 |
| Solan ELD | 0.1 |
| Methylparaben | 0.1 |
| Dekafald | 0.1 |
| 1,2-Propanediol | 0.1 |
| PVP/VA Copolymer 60/40 W | 10.0 |
| PP3 | 0.5 |
| N,N,N',N'-Ethylendiaminetetraacetate disodium salt | 0.01 |
| Sorbitol | 1.0 |

TABLE 2-continued

Hair gel

| Raw material | Wt % |
| --- | --- |
| D-Panthenol | 0.1 |
| Luviset Clear | 0.2 |
| Triethanolamine | 0.3 |
| Luviskol K 85 CQ solution | 5.0 |
| PEG-40 Hydrogenated Castor Oil | 0.4 |
| Perfume | 0.1 |
| Water | to 100 |

TABLE 3

Hair gel

| Raw material | Wt % |
| --- | --- |
| Dow Corning 9045 | 8.0 |
| Dow Corning 1501 Fluid | 8.0 |
| Simulgel EG | 2.0 |
| PP5 | 0.7 |
| 1,2-Propanediol | 1.7 |
| D-Panthenol | 0.2 |
| Herbasol distillate Seerose | 0.5 |
| 2-Phenoxyethanol | 0.5 |
| Dekafald | 0.1 |
| Luviskol K 85 CQ solution | 10.0 |
| Solubilisant LRI | 0.6 |
| Perfume | 0.1 |
| Water | to 100 |

TABLE 4

Hairspray

| Raw material | Wt % |
| --- | --- |
| Ethanol denatured with n-butanol/Bitrex ® | to 100 |
| AMP Ultra PC 1000 | 0.825 |
| Amphomer | 3.0 |
| PP1 | 0.3 |
| p-Methoxycinnamic acid isoamyl ester | 0.1 |
| Triethyl citrate | 0.1 |
| Isopropyl myristate | 0.05 |
| Perfume | 0.25 |
| Isobutane | 30 |

TABLE 5

Hair foam

| Raw material | Wt % |
| --- | --- |
| Hydagen HCMF | 0.3 |
| Lactic acid | 0.1 |
| Luviquat FC 370 | 1.0 |
| Celquat L-200 | 0.5 |
| Luviskol K 85 CQ | 2.0 |
| PP1 | 2.0 |
| Sodium benzoate | 0.3 |
| Benzophenone-4 | 0.1 |
| D-Panthenol | 0.1 |
| Glycerol | 0.2 |
| Genamin CTAC | 1.022 |
| PEG-40 Hydrogenated Castor Oil | 0.306 |
| Perfume | 0.102 |
| Propane/butane | 6 |
| Water | to 100 |

TABLE 6

Shampoo

| Raw material | Wt % |
| --- | --- |
| Texapon N 70 | 15.4 |
| PP3 | 4.0 |
| Sodium hydroxide | 0.14 |
| Citric acid monohydrate | 0.5 |
| Salicylic acid | 0.2 |
| Disodium cocoamphodiacetate | 7.0 |
| Arlypon F | 0.5 |
| Sodium benzoate | 0.5 |
| Euperlan PK 3000 AM | 2.6 |
| D-Panthenol | 0.1 |
| Nicotinic acid amide | 0.1 |
| Cutina HR | 0.1 |
| Cetiol HE | 0.8 |
| Polymer JR 400 | 0.3 |
| Co-enzyme Q 10 | 0.01 |
| Perfume | 0.1 |
| Sodium chloride | 0.5 |
| Water | to 100 |

Curl Retention—

The following compositions were prepared:

| A: | polyvinylpyrrolidone | 5 wt % |
| --- | --- | --- |
|  | water | 95 wt % |
| B: | polyvinylpyrrolidone | 5 wt % |
|  | PP6 | 1 wt % |
|  | water | 94 wt % |

Standardized hair strands of the Kerling company (item no. 827560), hair type "European Natural," color 6/0, with a length ($L_{max}$) of 220 mm and a weight of 0.6 g, were used. For preparation, the strands were washed with 12.5-wt % sodium laureth sulfate solution. The hair strands were dried overnight in a drying oven at 318 K. 0.18 g of the compositions was respectively applied onto each hair strand and massaged in. The strands were then wound onto a curler (Fripac-medis, diam. 7 mm, item no. D-1203) and dried overnight at room temperature.

The curlers were then carefully removed, and the strands were suspended. The length of each of the locks was measured ($L_0$), and the strands were put into a climate chamber. They were stored there at 294 K and a relative humidity of 85% for a period of 24 h, and the lengths of the locks were then measured again ($L_1$).

Five test strands were correspondingly treated and measured for each composition.

High humidity curl retention (HHCR) was calculated using the formula below, and the arithmetic mean of HHCR values for the five test strands was obtained for each composition:

$$HHCR = \frac{L_{max} - L_1}{L_{max} - L_0}$$

HHCR A: 38%

HHCR B: 43%

Addition of polyether-modified organic compounds according to the present invention results in an improvement in curl retention in high humidity.

We claim:

1. A cosmetic composition comprising, in a cosmetically acceptable carrier:
   (a) polyether-modified organic compounds that comprise at least three polyether substituents, the polyethers having a polyoxyalkylene chain made up of ethylene oxide units or of ethylene oxide units and propylene oxide units, having a maximum proportion of 50 wt % propylene oxide units based on weight of the polyoxyalkylene chain,
   wherein the polyether-modified organic compounds comprise a selected compound of formula (PE-1a) or (PE-1b) or (PE-1c) or (PE-1d) or (PE-1f):

(PE-1a)

(PE-1b)

(PE-1c)

(PE-1d)

(PE-1f)

$$T-K-(O-CH_2-CH)_m-(O-CH_2-CH_2)_p-$$
$$\qquad\qquad\quad|$$
$$\qquad\qquad CH_3$$

$$O-(CH_2-CH_2-O)_p-(CH-CH_2-O)_m-K-T$$
$$\qquad\qquad\qquad\qquad\qquad|$$
$$\qquad\qquad\qquad\qquad\qquad CH_3$$

$$—O\qquad O-(CH_2-CH_2-O)_p-(CH-CH_2-O)_m-K-T$$
$$\qquad\qquad\qquad\qquad\qquad\qquad|$$
$$\qquad\qquad\qquad\qquad\qquad\qquad CH_3$$

wherein for the selected compound:
at least three R groups are a —$(CH_2CH_2O)_p$—$(CHCH_3CH_2O)_m$—K-T group, and
the remaining R groups are a hydrogen atom or a —K-T group, wherein, mutually independently,
p is a whole number from 1 to 500,
m is a whole number from 0 to 500, and
p and m have a ratio to one another such that a maximum proportion of 50 wt % propylene oxide units, based on the weight of the corresponding polyoxyalkylene chain exists,
K is a covalent bond,
T has at least one substituent of —$Si(OR)_x(R')_{3-x}$ residue wherein
R and R' are, mutually independently, a ($C_1$ to $C_4$) alkyl group, and
x is 1, 2, or 3; and
(b) at least one film-forming and/or setting polymer.

2. A cosmetic composition comprising, in a cosmetically acceptable carrier:
(a) polyether-modified organic compounds that comprise at least three polyether substituents, the polyethers having a polyoxyalkylene chain made up of ethylene oxide units or of ethylene oxide units and propylene oxide units, having a maximum proportion of 50 wt % propylene oxide units based on weight of the polyoxyalkylene chain and chosen from at least one compound of formula (PE-1)

[Q—(—K'-A-K-T)$_n$]              (PE-1)

wherein
A is a polyoxyalkylene chain made up of ethylene oxide units or of ethylene oxide units and propylene oxide units, having a maximum proportion of 50 wt % propylene oxide units based on the weight of A,
K and K' are each a covalent bond,
T has at least one substituent of —$Si(OR)_x(R')_{3-x}$ residue wherein R and R' are, mutually independently, a ($C_1$ to $C_4$) alkyl group, and x is 1, 2, or 3,
Q is a C2-C30 hydrocarbon chain,
n is a whole number from 3 to 64, and
(b) at least one film-forming and/or setting polymer.

3. The cosmetic composition according to claim 2 comprising, in a cosmetically acceptable carrier:
(a) polyether-modified organic compounds obtained by reacting
at least 3 molar equivalents of at least one polyether of formula (I)

T-K-A-K'—Y              (I)

wherein
A is a polyoxyalkylene chain made up of ethylene oxide units or of ethylene oxide units and propylene oxide units, having a maximum proportion of 50 wt % propylene oxide units based on the weight of A,
K and K' are, mutually independently, a covalent bond,
T has at least one substituent of —$Si(OR)_x(R')_{3-x}$ residue wherein R and R' are, mutually independently, a ($C_1$ to $C_4$) alkyl group and x is 1, 2, or 3,
Y is a halogen atom, an isocyanate group, a carboxylic anhydride group, a halocarbonyl group, an epoxy group, or a formyl group, and
(b) at least one film-forming and/or setting polymer.

4. The cosmetic composition according to claim 1 comprising, in a cosmetically acceptable carrier,
(a) polyether-modified organic compounds that are obtained by reacting
at least 3 molar equivalents of at least one polyether of formula (III)

Y—K-T              (III), wherein
Y is a halogen atom, an isocyanate group, a carboxylic anhydride group, a halocarbonyl group, an epoxy group, or a formyl group,
K is a covalent bond,
T has at least one substituent of —Si(OR)$_x$(R')$_{3-x}$ residue wherein R and R' are, mutually independently, a (C$_1$ to C$_4$) alkyl group, x is 1, 2, or 3,
and
(b) at least one film-forming and/or setting polymer.

5. The cosmetic composition according to claim 1, wherein the polyether-modified organic compounds are present in an amount of from 0.01 to 10.0 wt %, based on total weight of the composition.

6. The cosmetic composition according to claim 2, wherein A includes a component of formula (A1)

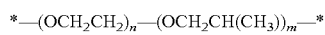   (A1)

wherein
n is a whole number from 1 to 500,
m is a whole number from 0 to 500, and
the component of formula (A1) has a maximum proportion of 50 wt % propylene oxide units, based on the weight of the component of formula (A1).

7. The cosmetic composition according to claim 2, wherein K and K' are, mutually independently, a covalent bond, a (C$_1$ to C$_6$) alkylene group, or at least one of the following connectivities (K1) to (K10)

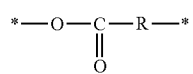   (K1)

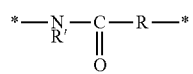   (K2)

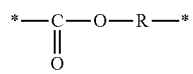   (K3)

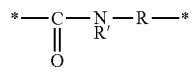   (K4)

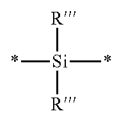   (K5)

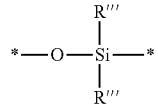   (K6)

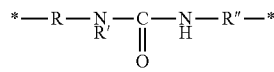   (K7)

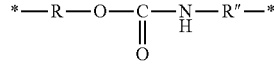   (K8)

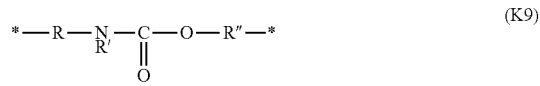   (K9)

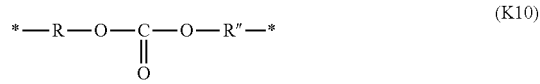   (K10)

in which

R and R" are, mutually independently, methylene, ethane-1,2-diyl, propane-1,2-diyl, propane-1,3-diyl, butane-1,2-diyl, butane-1,3-diyl, butane-1,4-diyl, or phenylene, R' is a hydrogen atom or a (C$_1$ to C$_4$) alkyl group, R''' is, mutually independently, a (C$_1$ to C$_4$) alkyl group or an aryl group.

8. The cosmetic composition according to claim 2,
wherein the polyether-modified organic compounds comprise a selected compound of formula (PE-1a) or (PE-1b) or (PE-1c) or (PE-1d) or (PE-1f):

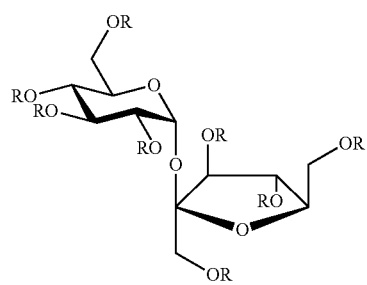   (PE-1a)

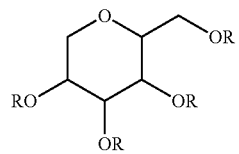   (PE-1b)

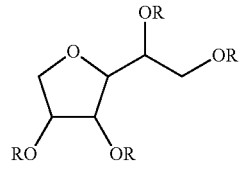   (PE-1c)

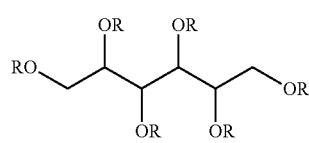   (PE-1d)

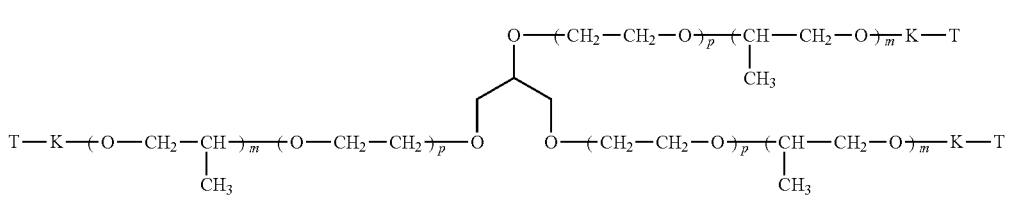
(PE-1f)

wherein for the selected compound:
at least three R groups are a —(CH$_2$CH$_2$O)$_p$—(CHCH$_3$CH$_2$O)$_m$—K-T group, and
the remaining R groups are a hydrogen atom or a —K-T group, wherein, mutually independently,
p is a whole number from 1 to 500 and m is a whole number from 0 to 500, and p and m have a ratio to one another such that a maximum proportion of 50 wt % propylene oxide units, based on the weight of the corresponding polyoxyalkylene chain, exists,
K is a covalent bond,
T has at least one substituent of
—Si(OR)$_x$(R')$_{3-x}$ residue
wherein R and R' are, mutually independently, a (C$_1$ to C$_4$) alkyl group, and x is 1, 2, or 3.

9. The cosmetic composition according to claim 2, wherein T conforms to the formula

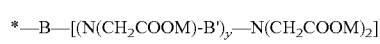

wherein
B is a (C$_1$ to C$_6$) alkylene residue,
B' is a (C$_1$ to C$_6$) alkylene residue or an N,N-bis(C$_1$ to C$_6$) alkylene-N-carboxymethyl,
M mutually independently is, a hydrogen atom or a metal cation of a metal from groups Ia, Ib, IIa, IIb, IIIb, VIa, or VIII,
y is 1 or 2.

10. The cosmetic composition according to claim 2, wherein T is a —Si(OR)$_x$(R')$_{3-x}$ residue wherein R and R' are, mutually independently, a (C$_1$ to C$_4$) alkyl group, and x is 2 or 3.

11. The cosmetic composition according to claim 1, wherein the film-forming and/or setting polymers are present in an amount of from 0.1 wt % to 20.0 wt %, based on total weight of the composition.

12. The cosmetic composition according to claim 1, further comprising as a film-forming and/or setting polymer at least one cationic film-forming and/or cationic setting polymer, at least one nonionic film-forming and/or nonionic setting polymer, at least one anionic film-forming and/or anionic setting polymer, and/or at least one amphoteric film-forming and/or amphoteric setting polymer.

13. A method of temporarily deforming hair comprising applying a composition according to claim 1 to hair.

14. A method of improving hairstyle hold comprising applying a composition according to claim 1 to hair.

15. The cosmetic composition according to claim 1 wherein T includes as at least one substituent a —Si(OR)$_x$(R')$_{3-x}$ residue wherein R and R' are, mutually independently, a (C$_1$ to C$_4$) alkyl group, and x is 1, 2, or 3.

16. The cosmetic composition according to claim 1 wherein the polyether-modified organic compounds comprises at least one compound of formula (PE-1a):

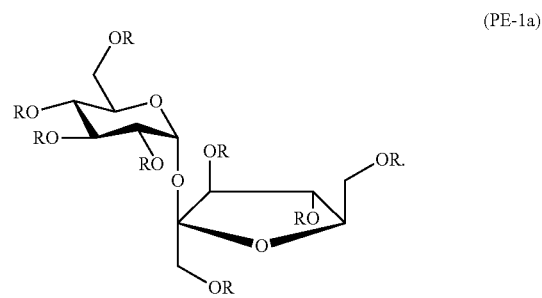
(PE-1a)

17. The cosmetic composition according to claim 1 wherein the polyether-modified organic compounds comprises at least one compound of formula (PE-1b):

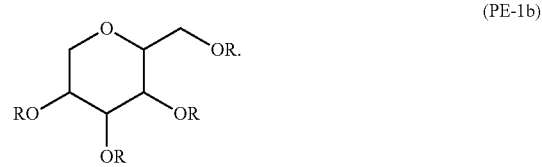
(PE-1b)

18. The cosmetic composition according to claim 1 wherein the polyether-modified organic compounds comprises at least one compound of formula (PE-1c):

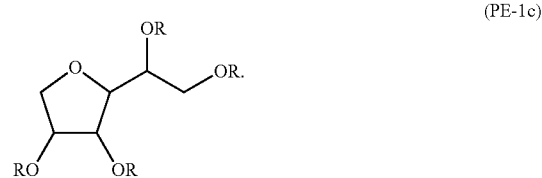
(PE-1c)

19. The cosmetic composition according to claim 1 wherein the polyether-modified organic compounds comprises at least one compound of formula (PE-1d):

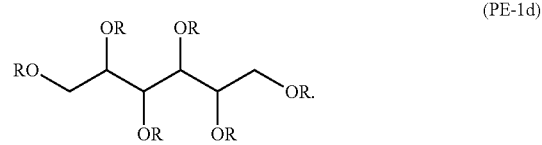
(PE-1d)

20. The cosmetic composition according to claim 1 wherein the polyether-modified organic compounds comprises at least one compound of formula (PE-1f):

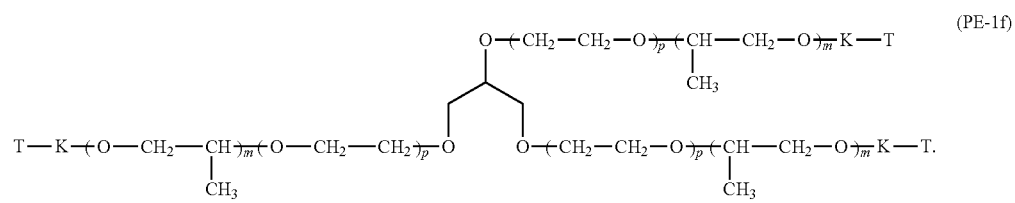
(PE-1f)
* * * * *